(12) United States Patent
Rosenthal et al.

(10) Patent No.: US 12,144,521 B2
(45) Date of Patent: **\*Nov. 19, 2024**

(54) NASAL DELIVERY TOOLS, SYSTEMS, AND METHODS OF USE

(71) Applicant: SPIROX, INC., Maple Grove, MN (US)

(72) Inventors: Michael H. Rosenthal, Maple Grove, MN (US); Scott J. Baron, Maple Grove, MN (US); Brian J. Domecus, Maple Grove, MN (US); Michael S. Mirizzi, Maple Grove, MN (US); Sergio Salinas, Maple Grove, MN (US)

(73) Assignee: Stryker Corporation, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/389,348

(22) Filed: Nov. 14, 2023

(65) Prior Publication Data

US 2024/0148408 A1 May 9, 2024

Related U.S. Application Data

(63) Continuation of application No. 17/882,837, filed on Aug. 8, 2022, now Pat. No. 11,877,771, which is a
(Continued)

(51) Int. Cl.
*A61F 2/18* (2006.01)
*A61B 17/00* (2006.01)
(Continued)

(52) U.S. Cl.
CPC .......... *A61B 17/3468* (2013.01); *A61F 2/186* (2013.01); *A61F 5/08* (2013.01);
(Continued)

(58) Field of Classification Search
CPC .............. A61M 37/0069; A61B 17/24; A61B 17/3468; A61F 5/08; A61F 2/186
See application file for complete search history.

(56) References Cited

U.S. PATENT DOCUMENTS

| 5,405,324 A | * | 4/1995 | Wiegerinck ....... A61M 37/0069 604/59 |
| 5,752,942 A | | 5/1998 | Dyle et al. |

(Continued)

FOREIGN PATENT DOCUMENTS

| JP | H06-007456 | 1/1994 |
| JP | 2011-500246 | 1/2011 |

(Continued)

OTHER PUBLICATIONS

English translation of Abstract of Japanese Patent Application No. 2016-067431 dated Apr. 29, 2022.
(Continued)

*Primary Examiner* — Majid Jamialahmadi
(74) *Attorney, Agent, or Firm* — McDonnell Boehnen Hulbert & Berghoff LLP

(57) ABSTRACT

A nasal implant delivery tool includes an inner handle, an outer handle, a needle, and a push rod. The inner handle includes a loading chamber configured to receive a nasal implant. The outer handle is configured to move axially relative to the inner handle. The needle extends distally from the inner handle and has a central lumen and a distal opening. The push rod is configured to move the nasal implant from the loading chamber, through the central lumen, and out the distal opening of the needle. The push rod is coupled to the outer handle such that the push rod moves axially relative to the inner handle when the outer handle is moved axially relative to the inner handle. Also described
(Continued)

herein are nasal implant guides and methods of using nasal implant delivery tools and nasal implant guides.

20 Claims, 35 Drawing Sheets

Related U.S. Application Data continuation of application No. 16/499,014, filed as application No. PCT/US2018/024932 on Mar. 28, 2018, now Pat. No. 11,464,542.

(60) Provisional application No. 62/477,829, filed on Mar. 28, 2017.

(51) Int. Cl.
*A61B 17/34* (2006.01)
*A61F 5/08* (2006.01)

(52) U.S. Cl.
CPC ............... *A61B 2017/0042* (2013.01); *A61B 2017/00853* (2013.01)

(56) References Cited

U.S. PATENT DOCUMENTS

| | | |
|---|---|---|
| 6,575,931 B1 | 6/2003 | Ponzi |
| 7,780,730 B2 | 8/2010 | Saidi et al. |
| 2006/0241650 A1 | 10/2006 | Weber et al. |
| 2011/0009872 A1 | 1/2011 | Mistry et al. |
| 2011/0251634 A1 | 10/2011 | Gonzales et al. |
| 2014/0243975 A1 | 8/2014 | Saidi et al. |
| 2015/0297213 A1 | 10/2015 | Lehtinen et al. |
| 2016/0058556 A1 | 3/2016 | Rosenthal et al. |
| 2017/0105836 A1 | 4/2017 | Baron et al. |
| 2019/0240005 A1 | 8/2019 | Rosenthal et al. |
| 2019/0343622 A1 | 11/2019 | Rosenthal et al. |
| 2020/0054446 A1 | 2/2020 | Rosenthal et al. |

FOREIGN PATENT DOCUMENTS

| | | |
|---|---|---|
| JP | 2016-067431 A | 5/2016 |
| WO | 2010017584 | 2/2010 |

OTHER PUBLICATIONS

International search report mailed on Aug. 8, 2018, issued in connection with International Application No. PCT/US2018/024932, filed Mar. 28, 2018, 4 pages.

Written Opinion mailed on Aug. 8, 2018, issued in connection with International Application No. PCT/US2018/024932, filed Mar. 28, 2018, 8 pages.

\* cited by examiner

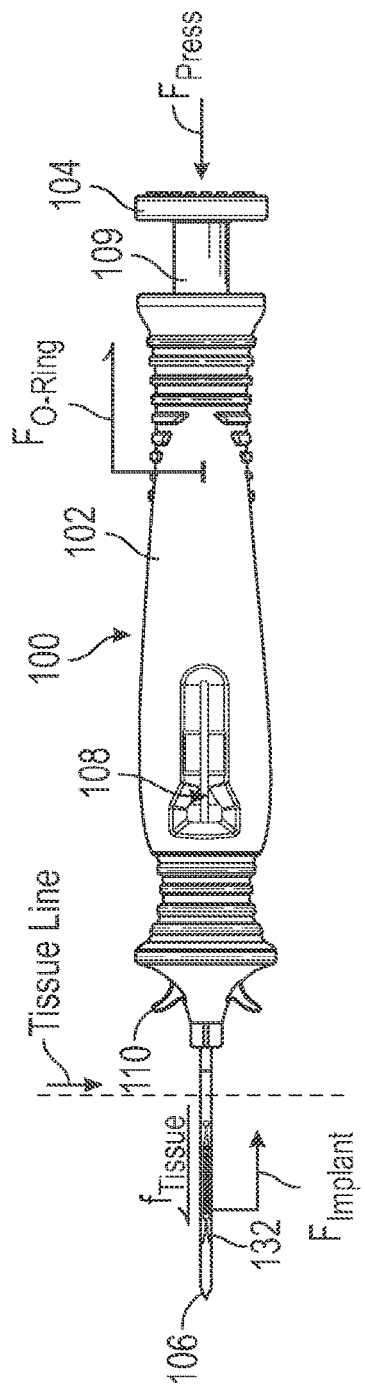
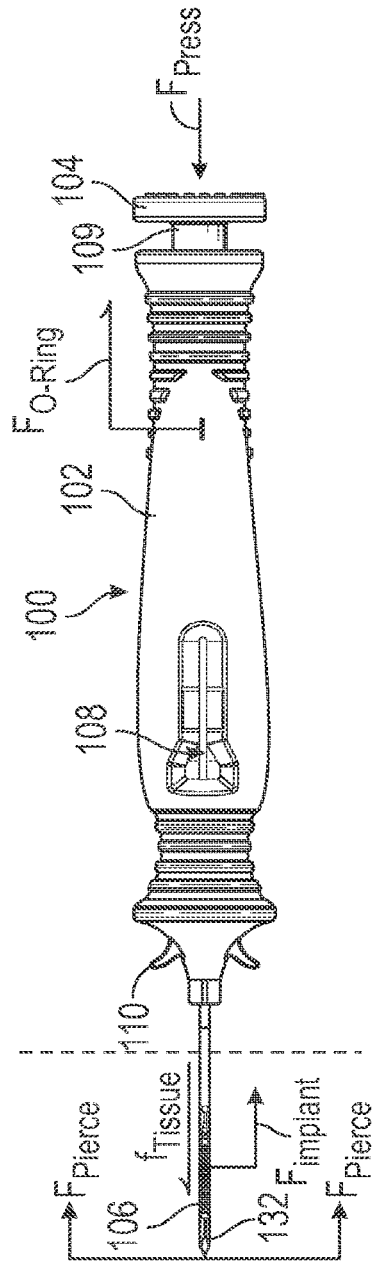
FIG. 2A
FIG. 2B

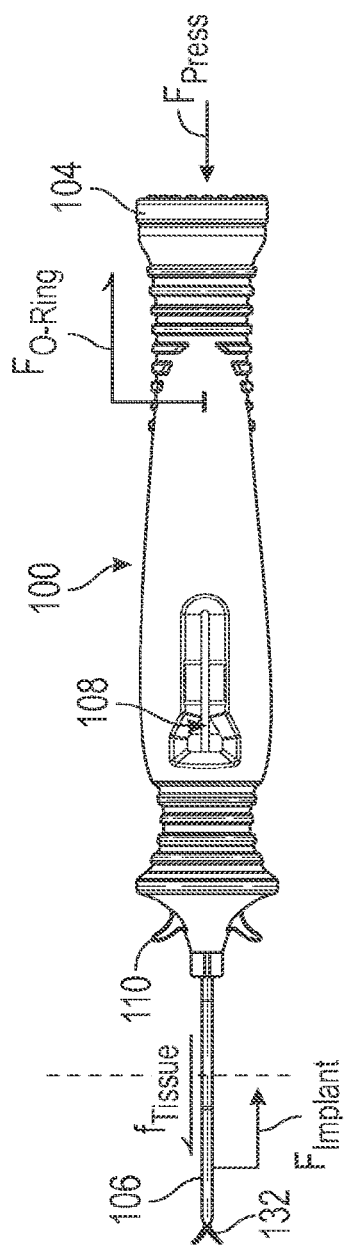
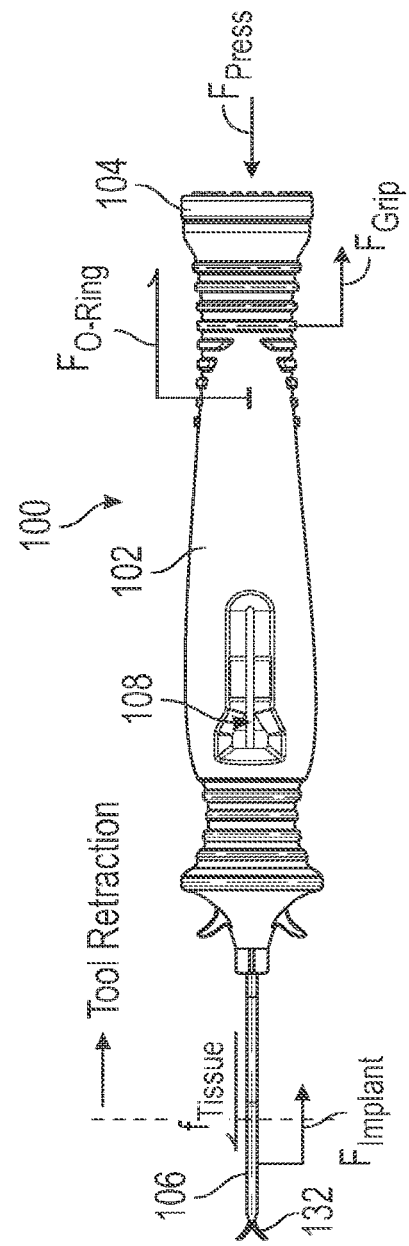
FIG. 2C
FIG. 2D

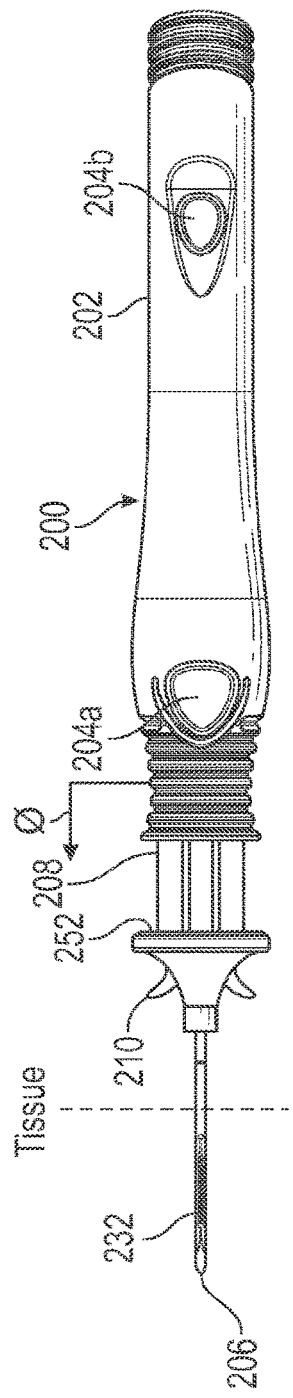
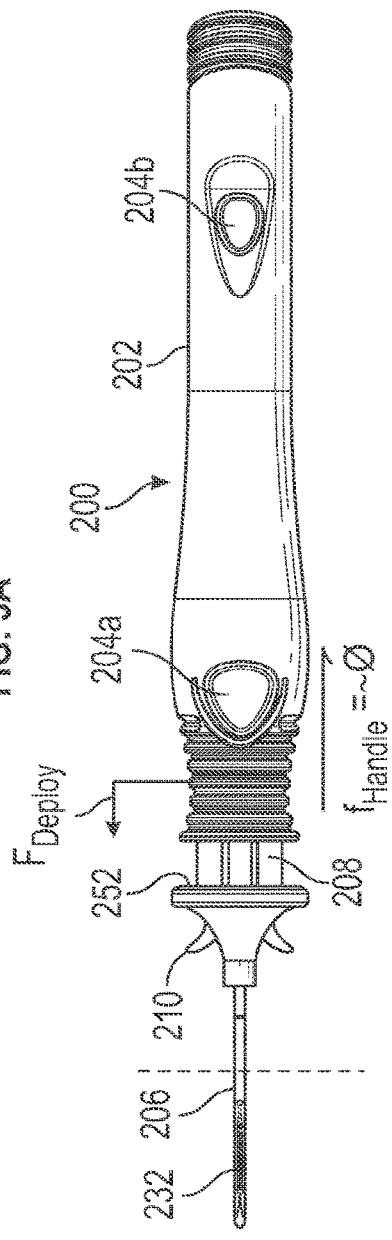
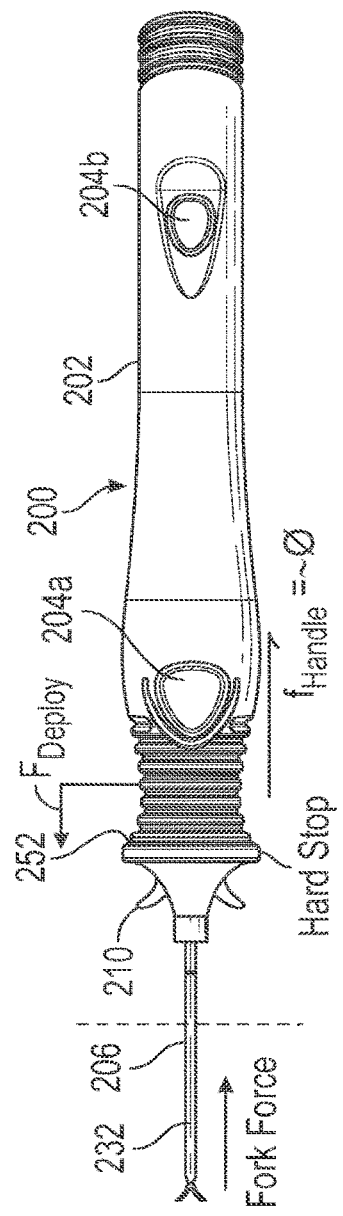
FIG. 3A
FIG. 3B
FIG. 3C

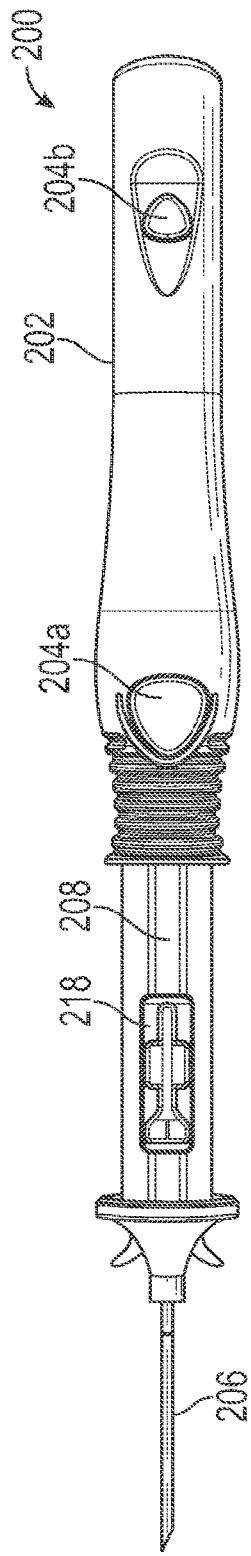
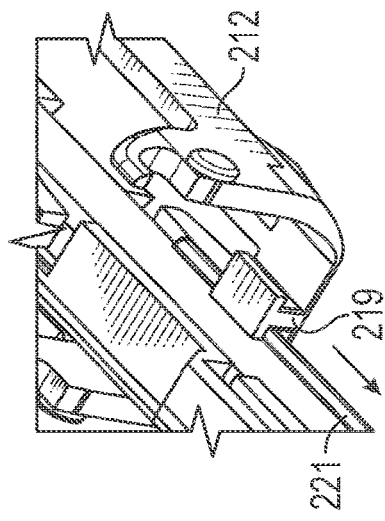
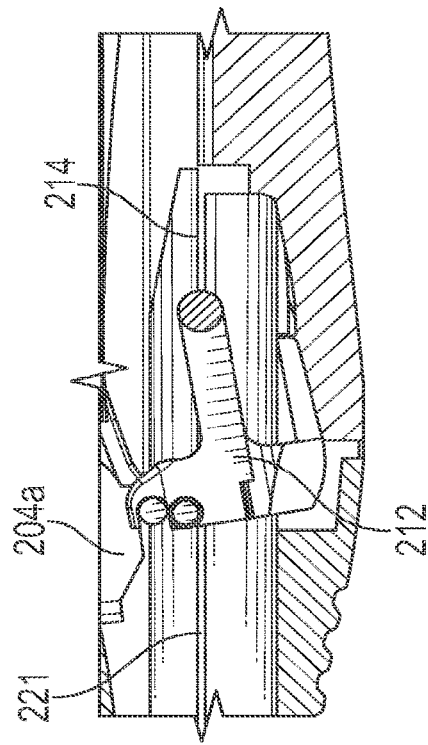
FIG. 5B
FIG. 5C
FIG. 5D

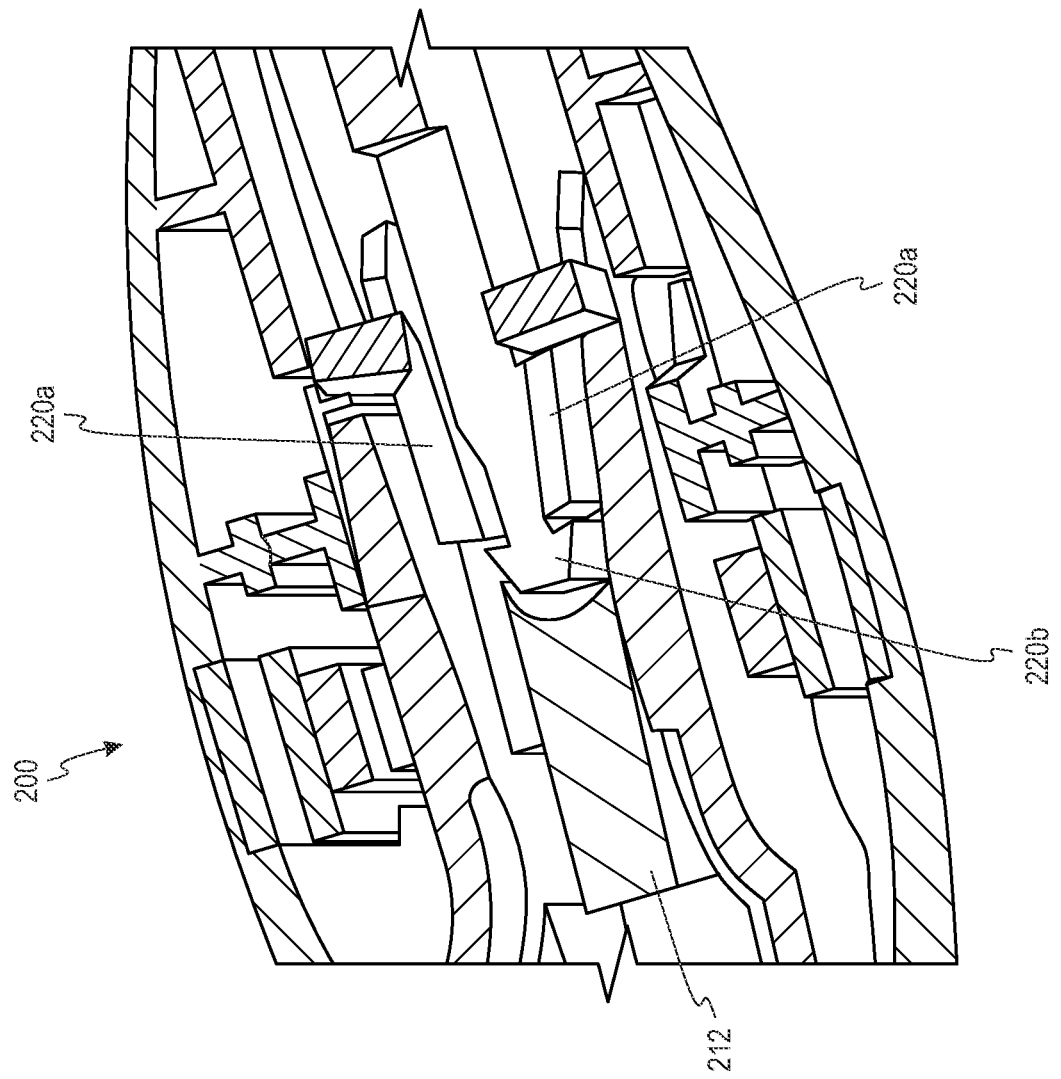

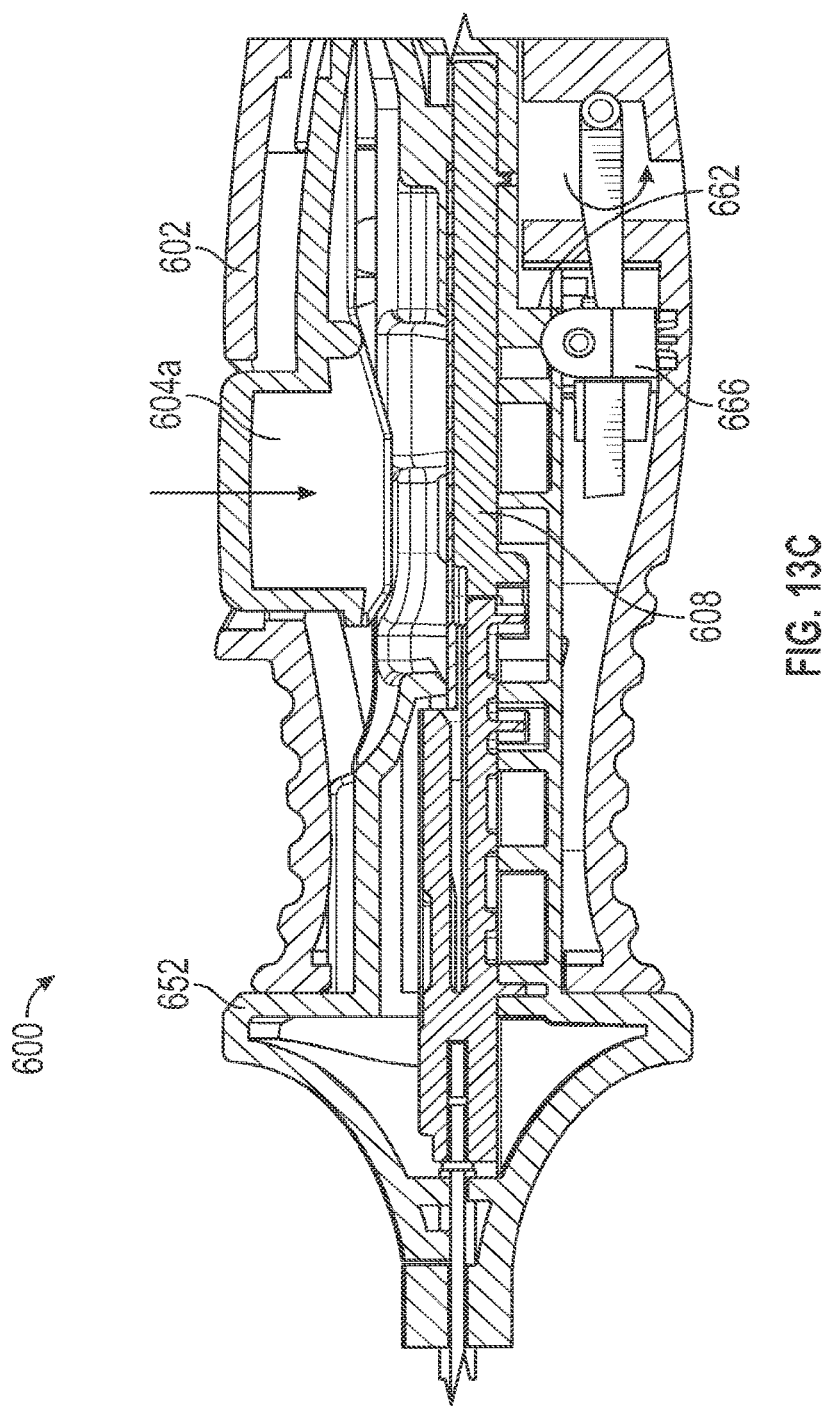

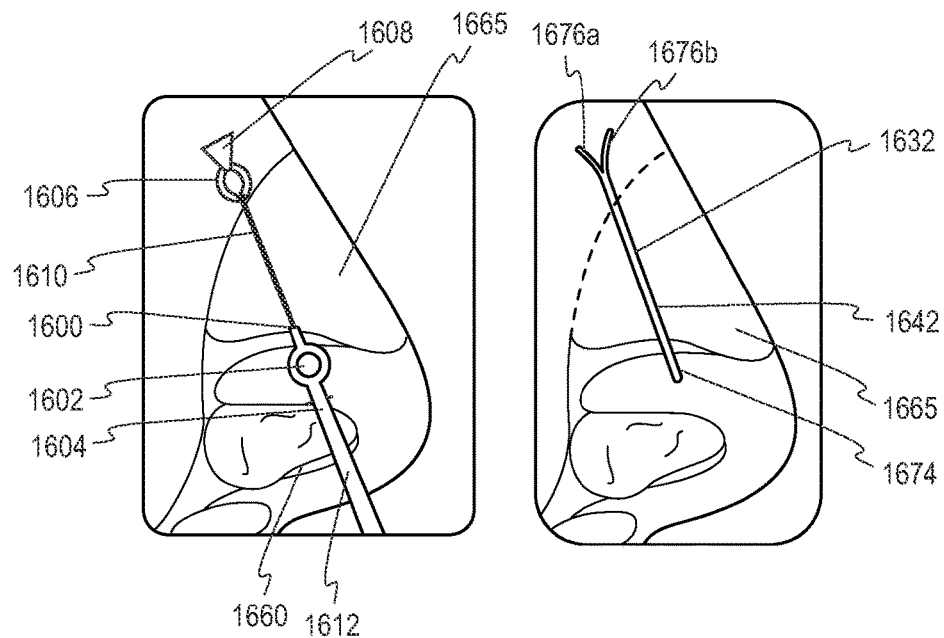
*Fig. 16A*  *Fig. 16B*
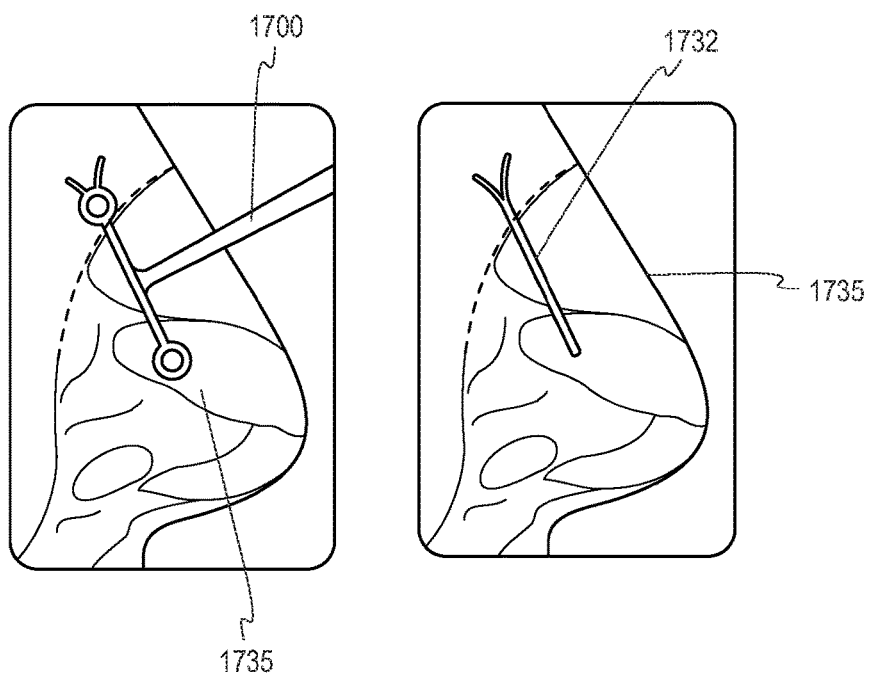
*Fig. 17A*  *Fig. 17B*

NASAL DELIVERY TOOLS, SYSTEMS, AND METHODS OF USE

CROSS REFERENCE TO RELATED APPLICATIONS

This application is a continuation of U.S. application Ser. No. 17/882,837, filed Aug. 8, 2022, which is a continuation of U.S. application Ser. No. 16/499,014, filed Sep. 27, 2019 (issued as U.S. Pat. No. 11,464,542), which is a national phase under 35 U.S.C. § 371 of International Application No. PCT/US18/24932, filed on Mar. 28, 2018, which claims priority to U.S. Provisional Application No. 62/477,829, filed Mar. 28, 2017, titled "NASAL DELIVERY TOOLS, SYSTEMS, AND METHODS OF USE", the contents of which are hereby incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are implants for placement in a body, tools for delivering the implants, and systems and methods for using the implants and tools. More particularly, described herein are nasal implants, tools for delivering nasal implants, and systems and methods for using such implants and tools.

BACKGROUND

The particular nasal anatomy of an individual may cause or contribute to various problems, such as cosmetic concerns, difficulty breathing, sleep apnea, or snoring, and can impact an individual's health or reduce the quality of life. For example, the structure of an external or internal nasal valve may resist airflow from the nose to the lungs and prevent an individual from getting sufficient oxygen to the blood.

Nasal valve collapse is a frequent cause of nasal airway obstruction, characterized by a loss of support from lateral nasal cartilages typically observed following rhinoplasty, nasal trauma, or age. Properly functioning nasal cartilage acts to keep the nasal passages open. If the lateral cartilages become weak, they collapse inward when a person inhales due to the negative pressure from the flow of air. This problem is currently largely untreated due to the complexity and highly variable results associated with current repair techniques, combined with the fact that a majority of patients are elderly or have a history of nasal surgery.

Overall, nasal valve collapse is an oftentimes untreated problem due to inconsistent results from a myriad of complex procedures performed by very few surgeons. As such, there remains a need for an endoscopic method to repair nasal valves in a simple, consistent manner. There is also a continued need for improvements to address problems attributed to nasal anatomy that are easy to use, long lasting, minimally invasive, low cost, and effective. There is also a continued need to improve the delivery of the nasal implant and for improved delivery tools for delivering nasal implants.

SUMMARY OF THE DISCLOSURE

Described herein are tools for delivering implants, systems including delivery tools and nasal implants, and methods for using the delivery tools for placing implants in a body. More particularly, described herein are nasal implants, tools for delivering nasal implants, and systems and methods for using such implants and tools. Also described herein are nasal implant positioning guides.

In general, in one embodiment, a nasal implant delivery tool includes an inner handle, an outer handle, a needle, and a push rod. The inner handle includes a loading chamber configured to receive a nasal implant. The outer handle is configured to move axially relative to the inner handle. The needle extends distally from the inner handle and has a central lumen and a distal opening. The push rod is configured to move the nasal implant from the loading chamber, through the central lumen, and out the distal opening of the needle. The push rod is coupled to the outer handle such that the push rod moves axially relative to the inner handle when the outer handle is moved axially relative to the inner handle.

This and other embodiments can include one or more of the following features. A distal end of the needle can include a flat bevel tip. A distal end of the needle can include a sharpened tip. The sharpened tip can include two or more surfaces having a bevel of 50 degrees or less. The outer handle can be configured to move between a plurality of discrete locking positions relative to the inner handle. The locking positions can correspond to a distal deployed position, a primed position, and proximal implant loading position. The push rod can be advanced distally such that the nasal implant is configured to be advanced partially or completely past the distal opening of the needle when the outer handle is in the distal deployed position. The central lumen of the needle can be configured to hold the nasal implant therein when the outer handle is in the primed position. The loading chamber can be exposed when the outer handle is in the proximal implant loading position. The delivery tool can further include a first button and a second button on the outer handle. The first button can be configured to allow the outer handle to move from the primed position to the distal deployed position when the first button is depressed. The first button can include a first locking feature configured to engage with a second locking feature on the inner handle to prevent the first button from being depressed when the outer handle is in the implant loading position. The second button can be configured to allow the outer handle to move from the primed position to the proximal implant loading position when the second button is depressed. The first button or the second button can include an engaging surface configured to engage with a corresponding engagement surface of the inner handle when the first or second button is not depressed. The first or second button can be configured to move the engaging surface when the first or second button is depressed such that the engaging surface disengages with the corresponding engagement surface of the inner handle to allow relative movement between the inner handle and the outer handle. The delivery tool can further include an implant orientation indicator configured to indicate an orientation of the nasal implant within the delivery tool. The implant orientation indicator can include a first arm projecting from the delivery tool in a first direction and a second arm projecting from the delivery tool in a second direction. The first arm and second arm can define a plane that can be substantially similar to the plane formed by a first arm and a second arm of the nasal implant in the deployed configuration. The needle can include a low friction coating on an external surface of the needle. The low friction coating can include PTFE, silicone, or poly(p-xylylene). The needle can include banded markings at various positions along the needle. The central lumen of the needle can include a portion having a non-circular cross-section. The outer handle can be configured to fully sheath a proximal end of the inner handle. The outer handle can include a grip configured to be manually held by a user.

In general, in one embodiment, a method of delivering a nasal implant to nasal tissue includes: (1) inserting a needle of a delivery tool into nasal tissue, where the delivery tool includes an inner handle housing a nasal implant therein; (2) advancing an outer handle of the delivery tool distally relative to the inner handle while maintaining a position of the inner handle so as to advance the implant distally through a needle of the delivery tool and into the nasal tissue; and (3) withdrawing the delivery tool from the nasal tissue.

This and other embodiments can include one or more of the following features. The implant can include a first arm at a distal end of the implant and a second arm at the distal end of the implant, the first arm moving away from a central longitudinal axis of the implant and the second arm moving away from the central longitudinal axis of the implant during the advancing step. Advancing the implant can include pushing the implant distally such that the first arm and second arm each engage the tissue. The method can further include advancing the outer handle to a distal locking position prior to withdrawing the delivery tool from the nasal tissue. The method can further include sliding the outer handle proximally relative to the inner handle to expose an implant loading chamber of the inner handle prior to inserting the needle. The method can further include loading the implant into the implant loading chamber of the delivery tool after the implant loading chamber is exposed. The method can further include pressing a button on the outer handle to unlock the outer handle from the inner handle prior to sliding the outer handle proximally to expose the implant loading chamber. The method can further include pressing a button on the outer handle to unlock the outer handle from the inner handle prior to advancing the outer handle of the delivery tool distally. The method can further include maintaining a known orientation between the implant and the needle during the inserting step. Maintaining the known orientation between the implant and the needle can include engaging the implant with a portion of a lumen of the needle having a non-circular cross section. The method can further include using a nasal implant guide to plan a position and an orientation of the nasal implant prior to inserting the needle.

In general, in one embodiment, a nasal implant guide includes a nasal implant guide portion and a handle. The nasal implant guide portion includes a proximal opening, a plurality of markings, a distal opening, and a forked feature. The proximal opening is configured to allow a mark to be made on the nasal lateral wall of a patient and corresponds to a proximal feature of a nasal implant. The plurality of markings are adjacent the proximal opening and are adapted to provide a ruler for a physician to judge a distance between the proximal feature and an alar rim edge. The distal opening is configured to allow a mark to be made on the nasal lateral wall of a patient and corresponds to a base of a distal fork of the nasal implant. The forked feature projects distally from the distal opening and corresponds to an expanded configuration of the distal forked feature of the nasal implant. The handle is engaged with the nasal implant guide portion and is configured to be hand graspable to position the nasal implant guide portion relative to the nasal lateral wall.

This and other embodiments can include one or more of the following features. The nasal implant guide portion can further include an image of a portion of a shape of the nasal implant. The handle can be engaged with the nasal implant guide portion such that the handle forms about a 90 degree angle to a dominant axis of the nasal implant guide portion. The forked feature can include a first projection and a second projection.

In general, in one embodiment, a system includes any of the delivery tools as described herein and a nasal implant as described herein. The system can further include any of the nasal implant guides described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D illustrate a delivery tool with a nasal implant at a plurality of positions. FIGS. 2A and 2B show a transparent view of the needle with the implant therein while FIGS. 2C and 2D show the end of the nasal implant extending from the needle and the rest hidden within the needle.

FIGS. 3A-3C illustrate another delivery tool with an implant at a plurality of positions. FIGS. 3A and 3B show a transparent view of the needle with the implant therein while FIG. 3C shows the end of the nasal implant extending from the needle and the rest still hidden within the needle.

FIG. 5B illustrates a top view of the delivery tool in the implant loading configuration. FIG. 5C illustrates a close-up of the latch mechanism in the implant loading configuration. FIG. 5D illustrates a locking mechanism in the implant loading configuration. FIG. 5E illustrates the hard stop in the implant loading configuration.

FIGS. 13A-13D illustrate a portion of a handle of another exemplary delivery tool.

FIGS. 14C-14D illustrate cross

FIGS. 16A-16B show use of an exemplary nasal guide to place an implant.

FIGS. 17A-17B show use of another exemplary nasal guide to place an implant.

DETAILED DESCRIPTION

Figure 1A:
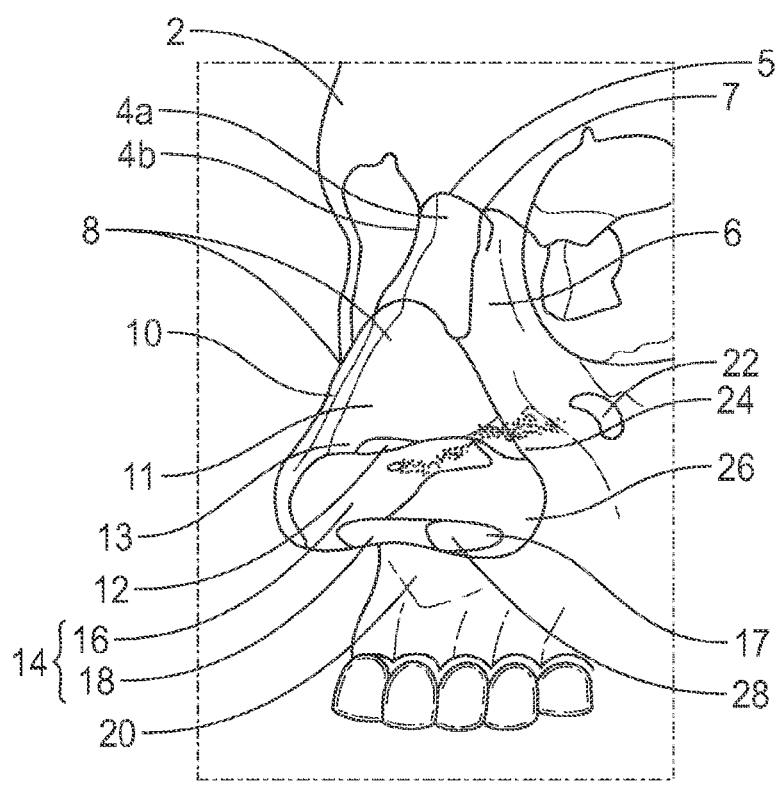
FIG. 1A shows the underlying structural nasal anatomy and tissues without overlying skin or tissue.

Described herein are nasal implants, delivery tools for delivering nasal implants, methods of using the implants, methods of using the tools to deliver a nasal implant, and external nasal guides to assist in placement of the nasal implants. The delivery tools, devices, systems, and methods described herein can provide various advantages and improvements. For example, the delivery tools can provide improved ergonomics and one handed use. The improved ergonomics can reduce the likelihood of incomplete nasal implant deployment and/or incorrect positioning of the nasal implant. The improved ergonomics can also make maintaining the positioning and orientation of the needle easier such that retraction of the tool is less likely to move the implant or change the orientation of the implant.

Embodiments of nasal implant delivery tools are described herein. In some embodiments, the nasal implant delivery tools include an inner handle including an implant loading chamber configured to receive a nasal implant and an outer handle configured to be hand graspable that is configured to move axially relative to the inner handle portion. The nasal implant delivery tools can include a needle extending distally from a portion of the inner handle with the needle. In some embodiments, the needle can have a non-circular cross-section. The non-circular cross-section can serve as an implant orientation feature such that the nasal implant traverses the lumen with a fixed and known rotational orientation. The device can include an opening or pathway between the implant loading chamber and the proximal end of the needle adapted to allow the implant to move from the implant loading chamber to a position within the needle. In one example, the needle can be adjunct to the loading chamber and a loading ramp which can compress the implant arms for entry into the lumen of the needle. The nasal implant delivery tool can include a plunging element/actuator (e.g., a push rod) configured to move the nasal implant from the loading chamber, into and along the needle lumen, and out of an opening at the distal end of the needle. The plunging element/actuator can be engaged with or coupled to the outer handle such that the plunging element/actuator moves axially relative to the inner handle portion with axial movement of the outer handle portion. The outer handle can be adapted to move between a plurality of discrete locking positions relative to the inner handle, e.g., using one or more buttons.

In some embodiments, the nasal implant delivery tool can include an implant orientation indicator configured to provide a visual indication of a plane formed by a first arm and a second arm of the nasal implant in the deployed configuration corresponding to the orientation of the implant within the needle lumen. The inner handle portion can include an implant orientation indicator configured to provide a visual indication of a plane formed by a first arm and a second arm of the nasal implant in the deployed configuration corresponding to the orientation of the implant within the needle lumen. The implant orientation indicator can be designed so that the operator of the tool can quickly see the orientation of the tool and the corresponding orientation of the plane formed by the arms of the nasal implant in the deployed configuration. The implant orientation indicator can extend from a portion of the handle such that the operator's hand does not cover or obscure the implant orientation indicator during use of the device. The implant orientation indicator can include a first arm projecting from the handle in a first direction and a second arm projecting from the handle in a second direction. The first arm and second arm can define a plane that is substantially similar to the plane formed by the first arm and the second arm of the nasal implant in the deployed configuration corresponding to the orientation of the implant within the needle lumen.

In some embodiments, the implant loading chamber is configured to receive a nasal implant in a deployed configuration. Further, the implant loading chamber can be adapted to move the nasal implant from an expanded configuration to a compressed delivery or primed configuration as the nasal implant is advanced into the needle lumen. A ramp between the implant loading chamber and the needle can be configured to move the arms of the implant to the compressed delivery configuration within the needle lumen.

In some embodiments, the needle includes a low friction coating on an external surface of the needle. In some examples, the low friction coating can be polytetrafluoroethylene (PTFE), silicone, or poly(p-xylylene). In some embodiments, the needle includes substantially banded markings at various positions along the needle. The banded markings can provide information to the physician relating to the depth and positioning of the needle within the nasal tissue.

In some embodiments, the nasal implant delivery tool can include the nasal implant therein. A implant can include any of the nasal implants described herein. In one example, a nasal implant for use with the loading tools described herein includes a body having a distal end, a proximal end, and a central portion disposed between the proximal end and the distal end. The implant further includes a first arm and a second arm. The first arm is disposed at the distal end and has a proximal end fixed to the body and a distal end not fixed to the body, and the distal end of the arm is adapted to move away from a central longitudinal axis of the body from a delivery configuration toward a deployed configuration. The second arm includes a proximal end fixed to the body and a distal end not fixed to the body, and the distal end of the second arm is adapted to move away from a central longitudinal axis of the body from a delivery configuration toward a deployed configuration. The first arm and second arms can define a plane when in the deployed configuration where the arms are away from the central longitudinal axis of the body.

Methods of supporting a tissue section of a patient's nose are also provided herein. In some embodiments, the method includes inserting a needle of a delivery tool as described herein into a tissue of the nose. The method can include advancing the outer handle distally to advance the implant distally from the needle lumen to place a distal end of the implant within the nasal tissue. The implant can include a first arm at a distal end of the implant and a second arm at the distal end of the implant. The method can include the first arm moving away from a central longitudinal axis of the implant during the advancing step, the second arm moving away from the central longitudinal axis of the implant during the advancing step. The method can include withdrawing the delivery tool from the nasal tissue and supporting the tissue section with the implant.

In some embodiments, the method can further include advancing the outer handle to a distal locking position prior to withdrawing the delivery tool from the nasal tissue. The use of the distal locking position can prevent the physician from advancing the outer handle incompletely because if the distal locking position is not reached, then the outer handle will slide during retraction informing the physician that the implant was not fully deployed. The method can further include sliding the outer handle proximally to expose the implant loading chamber of the inner handle portion. The method can also include pressing a button on the outer handle to unlock the outer handle from the inner handle portion prior to sliding the outer handle proximally to expose the implant loading chamber. Additionally, the method can include loading the implant into the implant loading chamber of the delivery tool. The loading step can include collapsing the first arm and second arm of the implant prior to entering the needle. The method can further include advancing the implant from the implant loading chamber into the needle lumen by advancing the outer handle and plunging element/actuator distally relative to the inner handle portion. Advancing the implant can include advancing the outer handle to a locking point followed by unlocking the outer handle prior to advancing the implant distally from the needle lumen to place the distal end of the implant within the nasal tissue. The method can include unlocking and advancing the outer handle portion independent of the inner handle portion while preventing needle and inner handle movement relative to the nasal anatomy. Unlocking the outer handle can include depressing a button on the outer handle to disengage the outer handle from a locking surface of the inner handle portion.

Systems are also described herein. The systems can include any of the delivery tools described herein and a nasal implant. The nasal implant can be any of the nasal implants described herein. The nasal implant can be within the needle or provided separately from the delivery tool. The systems can also include one or more of any of the nasal implant guides that are also described herein.

FIG. 1A shows the underlying structural anatomy and tissues of a face. The outer layers of overlying skin and muscle have been removed in the figure to better show the underlying cartilage and bone that provide structure. The nose sits in the middle of the face and provides olfaction (smelling) and respiration control (e.g., by restricting the flow of air). The nose has two airflow pathways, one on each side of the nose (starting with each nostril) which combine to form a single airflow pathway into the body. Air from the nose flows through the trachea and into the lungs where the air is spread out in the lobules of the lungs and oxygen is absorbed for use by the entire body. Each of the two airflow pathways in the nose have several segments including two types of nasal valves (called external nasal valves and internal nasal valves) along each nasal airflow pathway that act to control airflow through the nose. Together, the external and internal valves control airflow into and out of the body. The valves are tissues that surround the airflow, and the amount of resistance they provide to the airflow is determined largely by their shape and size (e.g., their internal cross-sectional area). The internal nasal valve on each pathway is the narrowest segment of the pathway in the nose and generally creates most of the resistance. Besides the important function of controlling airflow, the internal nasal valves also help give the nose its distinctive shape. The nasal valves are shaped and supported by various structures in the nose and face, with upper lateral cartilage playing a significant role in the form and function of the valves. Further, large or small changes in internal nasal valve structure can impair nasal breathing and/or can change the cosmetic appearance of the nose. Such changes generally act to reduce the cross-sectional area of the internal valve and can be caused by surgery, medical treatment, or trauma to the face. Additionally, there are variations of nasal valve structure between individuals, with some individuals having significantly narrowed valves due to weakened or misshaped cartilage, commonly observed as a pinched nose. A narrowed valve region can increase the acceleration of airflow and simultaneously decrease intraluminal pressure, causing the valves to collapse. While even normal nasal valves can collapse under great respiratory pressures, dysfunctional internal valves can collapse during normal breathing, resulting in reduced oxygen flow, snoring, and/or mouth breathing.

The nose includes the external nose that protrudes from the face and a nasal cavity underneath the external nose. From top to bottom, the external nose has a root, a bridge, a dorsum (ridge), a free tip (apex), and a columella. The external nose is appended to the piriform aperture, the continuous free edges of the pear shaped opening of the nasal cavity in the skull and is formed by the nasal bones and the maxilla. As shown in FIG. 1A, the nose sits in the middle of the face, framed by the bones of the head, with frontal bone 2 superior to the nose, lateral maxilla frontal process 6 lateral to it, and the maxilla anterior nasal spine 20 inferior to it (another lateral maxilla frontal process on the other side of the nose is not visible in this view). The external nose can be roughly divided into three layers from outside to inside: an overlying skin and muscle layer (removed in this view), a middle cartilage and bony framework layer, and an inner mucosal layer (not readily visible in this view).

While the middle cartilage and bony framework layer provides form, structure, and support to the nose, it also allows the nose to be flexible and wiggle and bend in different directions. The middle cartilage and bony framework layer can be roughly divided into three sections, including from top to bottom: an upper (superior) bony third and middle and lower (inferior) cartilaginous thirds. The upper third includes paired left nasal bone 4a and right nasal bone 4b that are joined in the middle of the nose and form the top (or superior) part of the bridge of the nose. Nasal bone 4a (along with lateral maxilla frontal process 6) joins frontal bone 2 superiorly to form the nasofrontal (nasion) suture line 5. Laterally, nasal bone 4a joins the maxilla at its frontal process 6 to form a fibrous joint at the maxilla nasal bone suture line 7 (or nasomaxillary suture line). The middle third of the cartilage and bony framework layer includes septal cartilage 10, which forms part of the septum of the nose and internally separates the nostrils and the two airflow pathways. Lateral process 8 of septal cartilage 10 merges superiorly with upper lateral cartilage 11 (another lateral process on the other side of the nose that merges with upper lateral cartilage on the other side of the nose is not visible in this view). FIG. 1A also shows minor alar cartilage 24, one of several accessory cartilages which provide support and allow movement of the nose, and which impact the complex 3-dimensional shape of the nose. Upper lateral cartilage 11 is normally fairly stiff and it has much of the responsibility for supporting the side of the nose. In conjunction with septal cartilage tissue, it helps to form the internal nasal valve, which is inside the nose under the upper lateral cartilage and not readily visible in this view.

As mentioned above, there are two internal nasal valves (one on either side of the nose). Each internal nasal valve is formed by and bordered medially by septal cartilage 10, laterally by the caudal margin 13 of the upper lateral cartilage, and inferiorly by the head of inferior turbinate (not visible in this view). The attachment of the upper lateral cartilage to the septum (septal cartilage) forms an angle that defines the internal nasal valve angle (also called simply "valve angle"). The internal nasal valve angle is the narrowest part of the nasal airway and creates resistance that controls airflow through it. There is some natural variation between individuals in their nasal valve angles, and valve angles may change over time as a natural consequence of aging. Valve angle is determined in part by genetics, and an ethnic group has a particular average valve angle associated with it. There is also variation in valve angles between individuals, even within a particular ethnic group, and between an individual's left and right valves. Nasal valve angles may also be altered as a result of surgery, trauma or another intervention. A valve with a valve angle of less than about 10 degrees may generally be considered collapsed, causing nasal airway obstruction with nasal sidewall collapse upon inspiration and may merit treatment such as described herein. A valve angle that is greater 10 degrees may also cause some airway obstruction and/or cosmetic concern and may also merit treatment but its dysfunction is generally not as severe as a collapsed valve. Valves in need of treatment may be candidates for treatment using the implants, devices, systems and methods described herein.

The lower third of the cartilage and bony framework layer includes major alar cartilage (also referred to as lower lateral cartilage or inferior lateral cartilage, based on its location and to distinguish it from upper lateral cartilage) that help shape the nostrils and the tip of the nose. This cartilage is softer and more mobile than upper lateral cartilage, and it allows the tip of the nose to move. Major alar cartilage 14 is u-shaped and includes lateral crus 16 and medial crus 18. Major alar cartilage 14 forms part of external valve around nostril 17 (also called nares), though it does not quite reach the bone laterally. The lower third of the cartilage and bony framework layer also includes alar fibrofatty tissue 26 of alar that fills the gap between lateral crus 16 and the bone. FIG. 1A also shows small accessory alar cartilage 12 that links the major alar and lateral cartilage 8 of the cartilage and bony framework layer.

As mentioned above, the nose is a complex, 3-dimensional structure. It may be desirable to change its shape or better support its structure in order to improve or maintain its function or appearance (cosmesis), but it can difficult to change one aspect of the nose without adversely affecting another part. Indeed, previous surgical interventions are one cause of altered nasal valve function that may be treated using the systems and methods described herein. Described herein are implants, devices, systems and methods function for changing or supporting an aspect of a body structure or shape, including of the nose.

Figure 1B:
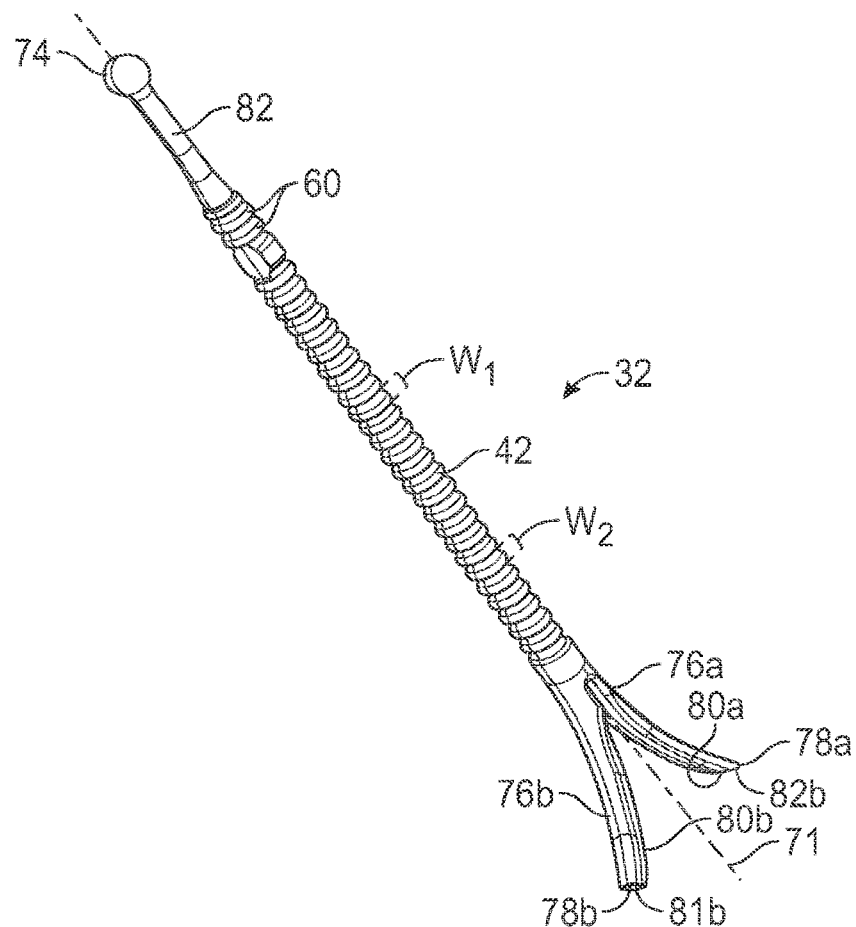
FIGS. 1B and 1C show an exemplary nasal implant.
Figure 1C:
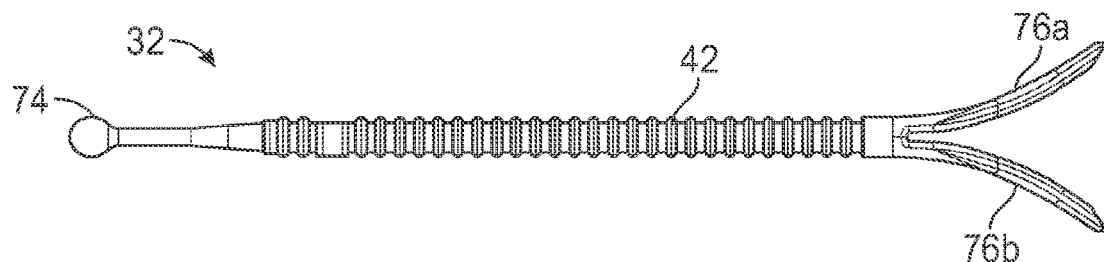

An exemplary nasal implant 32 (e.g., for use with a delivery tool as described herein) is shown in FIGS. 1B-1C. The implant 32 includes a central body having a first arm 76a and a second arm 76b each having respectively, first arm outer bevel 78a and second arm outer bevel 78b, on radially outward surfaces of a distal end of implant 32. The outer bevels 78a,b may be useful, for example, for guiding an implant into a delivery device, for contracting an implant into a contracted configuration, for orienting an implant in a delivery device, or for guiding an implant through a delivery device. The first and second arms 76a,b can additionally include inner bevels 80a,b. In some embodiments, the inner bevels 80a,b and outer bevels 78a,b can form a double bevel. The inner bevels 80a,b and outer bevels 78a,b can share an edge (e.g., the two slanted surfaces can meet each other at any angle but 90°) or may flare away from each other. In some examples, the inner bevels 80a,b and outer bevels 78a,b can meet another at any angle but 90° and not share an edge (e.g., the bevels can be formed from different edges). The bevels 78a,b and 80a,b may be at an end of an arm or protrusion or along a side of a projection or protrusion.

The implant 32 can further include a proximal feature 74 at the proximal end. The proximal feature 74 can be a rounded atraumatic blunt end (as shown), a sharp end, or a flat end The atraumatic proximal feature 74 may prevent the proximal implant end from damaging, cutting, or exiting a tissue when it is in place in the tissue, such as in a nasal tissue. The proximal feature 74 may help to anchor or otherwise hold an implant in place in the tissue in which it is implanted.

The implant 32 can also include strain relief section 82 just distal to the proximal feature 74. As shown, the strain relief section 82 can have a relatively smaller cross-sectional area (e.g., a diameter) than other portions of the implant 32. In some embodiments, the strain relief section 82 may be larger than another area, but still provide strain relief by having a different configuration or a different material.

The implant 32 can also include a central bridging region 42 between the distal arms 76a,b and the proximal feature 74. The central bridging region 42 can be especially useful for bridging an area in need of support, such as weak or collapsed area between structures on either (both) ends. For example, the central bridging region 42 may bridge a weak or collapsed nasal valve in a nose. The central region 42 may include one or more ribs (also called ridges) 60. The ribs 60 can help anchor the implant 32 in place, such as by catching tissue against the ribs 60 or valleys therebetween. As shown in FIG. 1B, a first rib 60 has a first rib width W1 and a second rib 60 has a second rib width W2. Rib widths W1 and W2 may be the same size or may be different sizes. The first rib 60 may have a first rib diameter and the second rib 60 may have a second rib diameter. The first and second rib diameters may be the same size or may be different sizes. The implant 32 can additionally include one more other body features, such as bevels, scallops, or wings.

Implants similar to implant 32 are described in US 2016-0058556, the entirety of which is incorporated by reference herein.

Figure 1D:
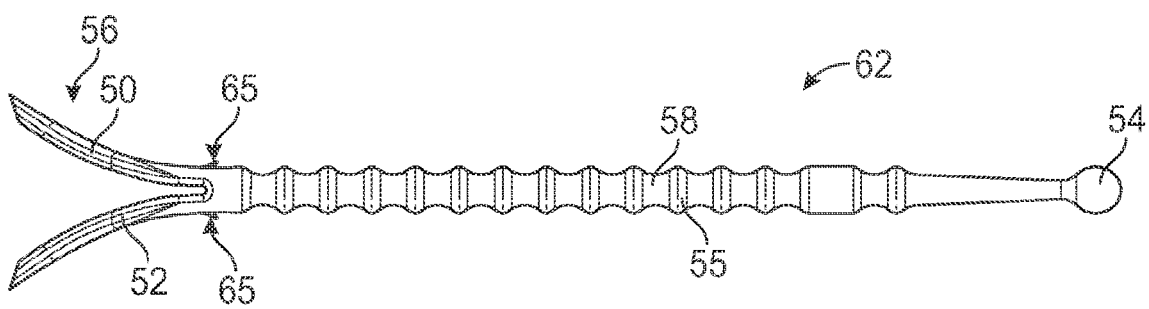
FIG. 1D illustrates another exemplary nasal implant.

FIG. 1D illustrates another embodiment of a nasal implant 62. The implant 62 includes a central body 58, a distal end 56 with two forked arms 50, 52, and an atraumatic proximal end 54. The implant 62 includes two barbs 65 at the portion of the implant where the arms 50, 52 meet the central body 58. The barbs 65 extend transversely to the plane defined by the forked arms 52, 50. The barbs 65 extend from two opposing sides of the implant and can be molded or skived. Additionally, the central body 58 can include a series of ribs 55 therearound. Implants similar to implant 62 are described in International Application No. PCT/US17/68419, filed Dec. 26, 2017, titled "NASAL IMPLANTS AND METHODS OF USE," the entirety of which is incorporated by reference herein.

Figure 1E:
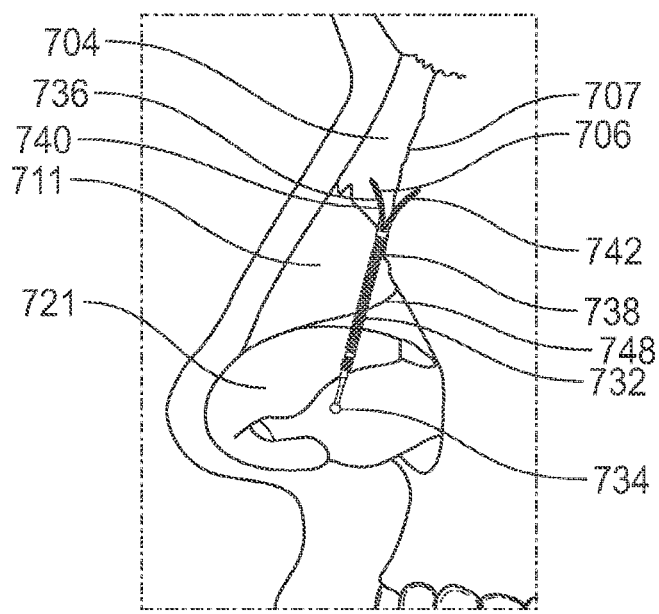
FIGS. 1E and 1F show placement of a nasal implant in the nasal anatomy.
Figure 1F:
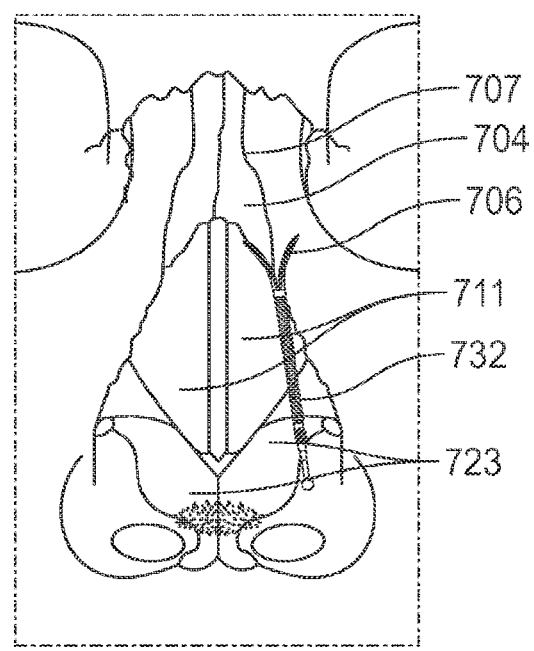

FIGS. 1E and 1F show front and side views, respectively, of an implant 732 (which can be, for example, the same as implant 32 or implant 62) implanted in a patient's nose (e.g., with delivery tools as described herein) and supporting a tissue section of a patient's nose. The implant 732 may be useful for maintaining or improving nasal function or appearance and can underlie the skin and muscles (which have been removed in the figures to better illustrate the implant and the underlying nasal structures and implant). FIGS. 1E and 1F show the implant 732 in place for supporting or changing an internal nasal valve. The implant 732 thus apposes structures in the cartilage and bony framework layer under the skin and muscle. The implant 732 has a body with a proximal end 734, a distal end 736, and a central portion 738 between the proximal and distal ends. The central portion 738 is in a position between the nasal cartilage and patient skin or muscle. The central portion 738 further apposes upper lateral cartilage 711 and lower lateral crura 721 of the lower lateral cartilage 723. As mentioned above, along with the septal cartilage, the caudal end of the upper lateral cartilage defines the internal valve angle, and central portion 738 of implant 732 also apposes the caudal end 748 of the upper lateral cartilage 711 and so overlies or acts on the internal valve wall, providing support to or changing a shape of the internal valve. The distal end 736 of implant 732 apposes structures in the upper part of cartilage and bony framework. The arms 740, 742 appose nasal bone 704, frontal process 706 of the maxilla bone, and maxilla nasal bone suture line 707 (nasomaxillary suture line). In some variations, a distal end of an implant may be apposed or in proximity to one of more structures in the upper layer or any of the structures or tissues in the middle or lower cartilage and bony framework layer (e.g., accessory cartilage, major alar cartilage, minor alar cartilage, septal cartilage, maxilla, etc.).

In some embodiments, specialized tools can be used to deliver the implants (e.g., implants 32, 62, 732) into the nasal tissue.

Referring to FIGS. 2A-2C, a delivery tool 100 can be used to deliver implant 132 (which can be any of the implants described herein). The delivery tool 100 includes a hand graspable handle 102, a needle 106 extending from the handle 102, and a plunger 104 attached to a push rod 109 and adapted to advance the nasal implant 132 within the needle 106. In some embodiments, the needle 106 can include a non-circular cross-section that can allow the implant to align properly within the needle 106 (e.g., the arms of the implant can diverge slightly in the outward direction of the major axis to orient the implant 132 within the needle 106). Further, handle 102 can include implant orientation features 110. When the implant 132 is properly positioned within the needle 106, the implant orientation features 110 can be oriented along the same longitudinal axis as the arms or forks of the implant 132 when the arms are in the expanded configuration. The orientation features 110 can thus help the user visualize the plane defined by the arms of the implant 132 in the expanded configuration. In some embodiments, the handle 102 can include an implant loading window 108 that allows viewing of the implant 132 through the handle 102 when the device 100 is in the primed (ready) position. Additionally, in some embodiments, the delivery tool 100 can include a plunger o-ring therein that can be configured to provide low, consistent friction throughout the deployment of the plunger 104 (i.e., to keep the deployment smooth) and to help keep the plunger 104 from moving unintentionally if the tool 100 is moved.

FIGS. 2A-2C show the stages of the proper deployment of the implant 132 from the tool 100. During Phase 1 of the deployment (FIG. 2A), the force the user applies to the plunger 104 ($F_{PRESS}$) can correspond to a force that overcomes the minimal friction of the implant 132 sliding within the needle 106 ($F_{IMPLANT}$) and the friction of the push rod 109 within the tool 100, i.e., along the O-ring ($F_{O\text{-}RING}$). The plunger force can be low and constant as the implant 132 starts to exit the needle 106 and interact with the nasal tissue. During Phase 2 of the deployment (FIG. 2B), the forked arms of the implant 132 begin to exit the distal end of the needle 106 and interact with the adjacent nasal tissue. This generates a force ($F_{PIERCE}$) that translates straight to the plunger 104. As a result, $F_{PRESS}$ becomes greater until the forks of the implant 232 pierce into the tissue. During Phase 3 (FIG. 2C), when deployed correctly, the user continues to depress the plunger 104 at the higher force ($F_{PRESS}$) until the plunger 104 reaches its end of travel, e.g., until the plunger 104 hits the proximal end of the handle 102. In some embodiments, the tool 100 can be held stationary relative to the tissue while the forked arms of the implant 132 pierce into the tissue about 4 mm beyond the distal tip of the needle 106.

FIG. 2D shows improper deployment of the implant 232 from the tool 100. In order to provide counter traction while applying $F_{PRESS}$, users sometimes support the device 100 by grabbing the housing of the tool e.g. the main handle body 102. Supporting the device 100 here can have a force reaction $F_{GRIP}$ as the user attempts to counteract the force $F_{PRESS}$ by pulling proximally on the handle 102. As a result, the implant 132 can be held stationary while the tool 100 is retracted proximally from the tissue. This can result in the implant 132 not reaching its desired or intended position and potentially about 4-6 mm caudal to (delivered short of) the desired location. To the untrained eye, this reaction may not even be detected during the deployment and can feel just like a correct deployment. However, this incorrect placement can require removal of the implant 132 or result in the implant 132 not properly supporting the nasal tissue in the desired manner. Thus, in some embodiments, a delivery tool can be configured to prevent or minimize the chance of inadvertent retraction during deployment.

Figure 3D:
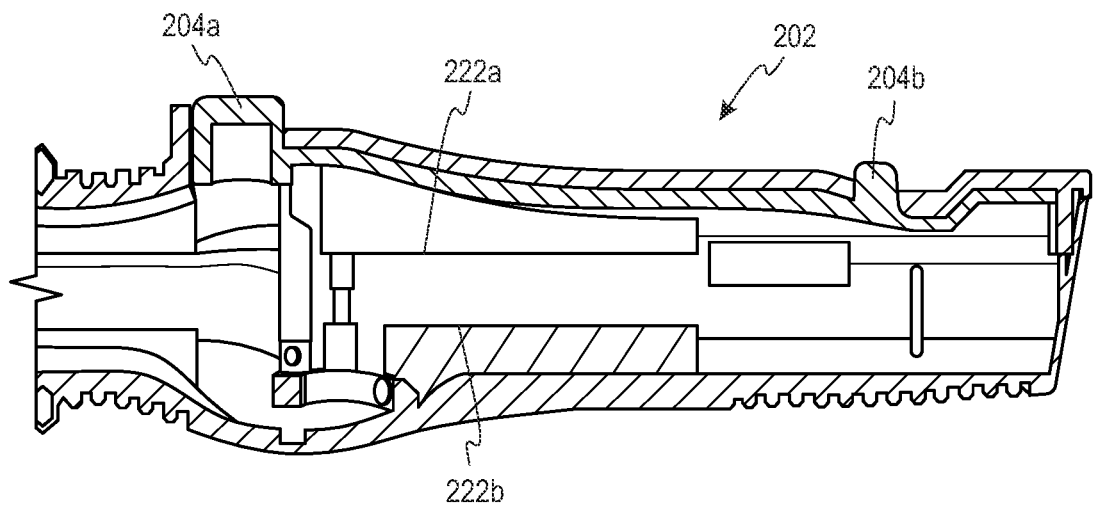
FIG. 3D shows a cross section of the outer handle of the device of FIGS. 3A-3C taken along the longitudinal axis.
Figure 3E:
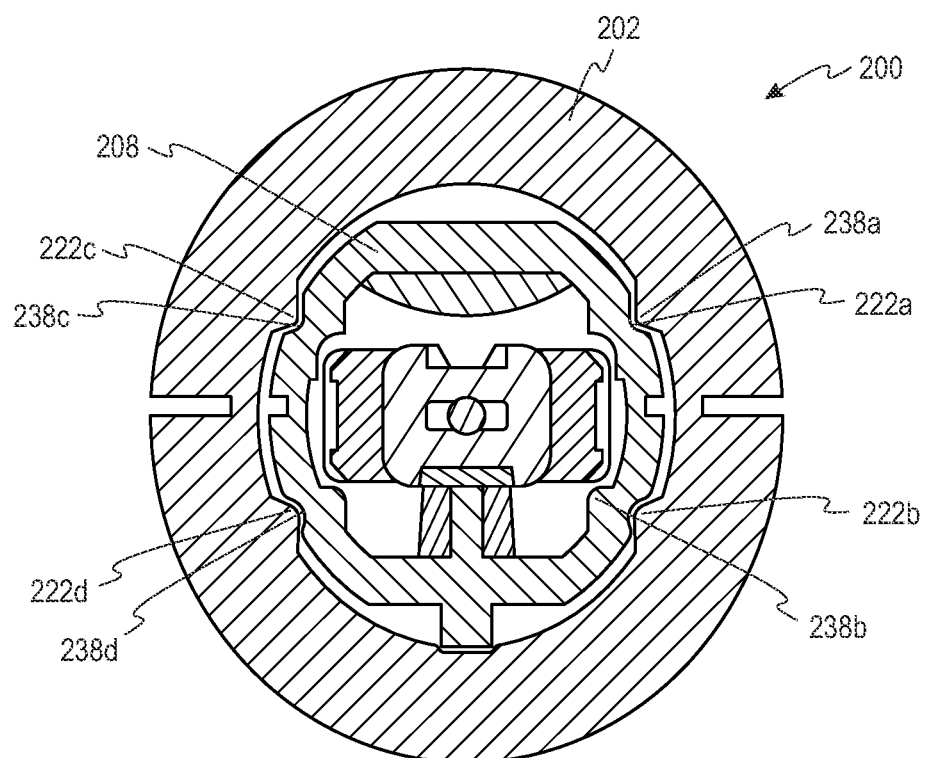
FIG. 3E shows a cross-section of a device of FIGS. 3A-3C taken perpendicular to the longitudinal axis.
Figure 3F:
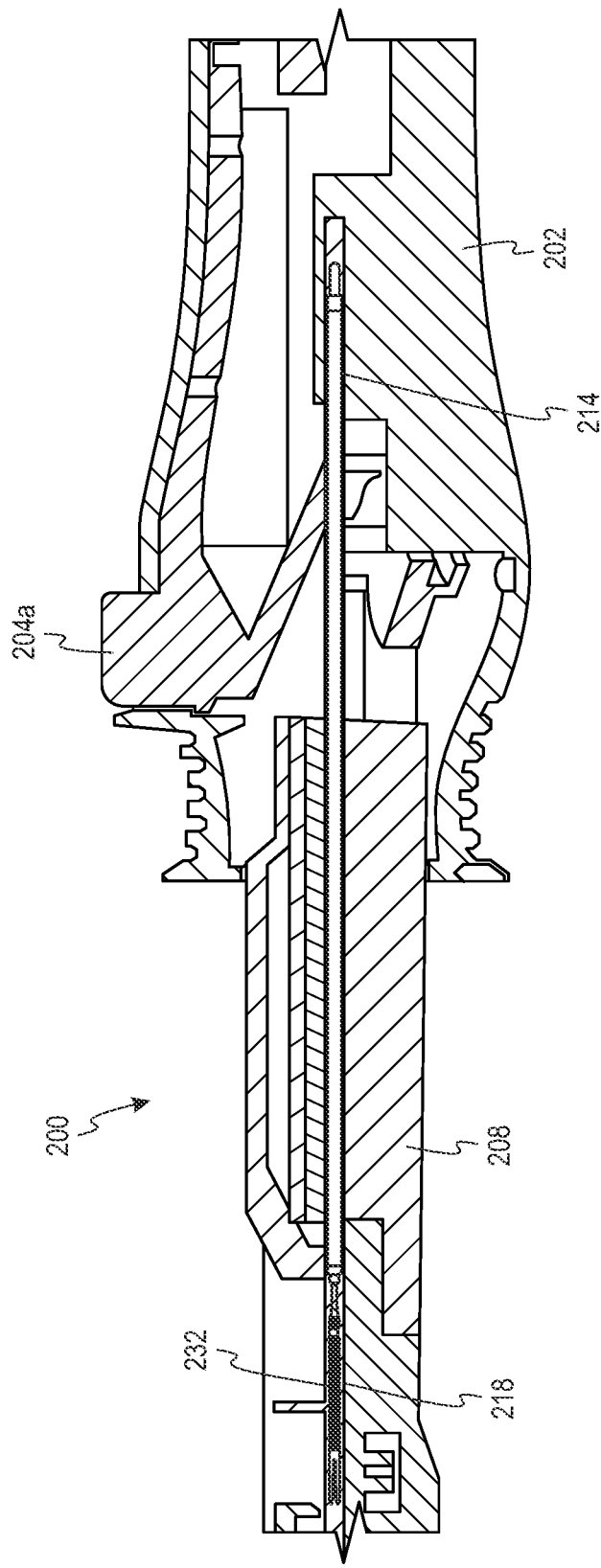
FIG. 3F show a cross-section of a central portion of the entire device of FIGS. 3A-3C taken along the longitudinal axis.

FIGS. 3A-3F illustrate an embodiment of a delivery tool 200 that can help prevent or minimize the chance of inadvertent retraction during deployment. The delivery tool 200 includes a hand graspable outer handle 202, an inner handle 208, and a needle 206 (e.g., with a portion having a non-circular cross-section as described with respect to delivery tool 100). The outer handle 202 is slideable relative to the inner handle 208 and includes a distal button 204a and a proximal button 204b. The inner handle 208 has a flange 252 and the distal end thereof, orientation features 210, and an implant loading window in some embodiments. As shown in FIGS. 3D-3E, bearing surfaces 238a-d on the inner handle 208 can slide along rails 222a-d on the inner surface of the outer handle 202 to allow the sliding motion between the inner handle 208 and the outer handle 202. The rails 222a-d can span 50-80%, such as approximately 60%, of the length of the outer handle 202 while the bearing surfaces 238a-d can span substantially the entire length of the inner handle 208. Like tool 100, the implant orientation features 210 of tool 200 can be positioned so as to align longitudinally with the arms of the implant 232 (which can be any implant described herein).

The nasal implant 232 can be advanced through the needle 206 by advancing the outer handle 202 distally relative to the needle 206. The outer handle 202 is rigidly connected to a push rod 214 (see FIG. 3F), which provides force to the implant 232 to move it distally through the needle 206 when the outer handle 202 is moved distally over the inner handle 208. The distal button 204a can be configured to be depressed to allow distal movement of the outer handle 202 relative to the inner handle 208. Further, the proximal button 204b can be configured to be depressed to allow release of the outer handle 202 from the inner handle 208 such that the outer handle 202 can move proximally relative to the inner handle 208 to allow loading of the implant 232.

FIGS. 3A-3C show the stages of deployment of the implant 232 with the tool 200. At FIG. 3A, the implant 232 is loaded in the needle 206 and ready for deployment. No deployment of the implant 232 can occur until the user depresses the distal button 204a. At FIG. 3B, the tool 200 illustrates partial deployment of the implant 232. The distal button 204a is in the depressed position, thus disengaging the inner handle 208 from the outer handle 202. Similar to device 100, the force to deploy the implant 232 will be low until the forked arms of the implant 232 begin to engage the tissue. At this point, the force to advance the outer handle 208 and implant 232 will increase until the forked arms pierce into the soft tissue. The deployed configuration of the delivery tool 200 with the implant 232 deployed in the tissue is shown in FIG. 3C. As the outer handle 202 slides forward relative to the inner handle 208, the forked arms of the implant 232 will be pushed distally out of the needle 206 and into the tissue. When the outer handle 202 extends completely over the inner handle 208, the outer handle 202 can come to a hard stop (i.e., against the flange 252) and lock in the stopped position. When the outer handle 202 is fully advanced, the handle can lock in place with an audible and tactile click detectable by the user. If the outer handle 202 is not advanced fully to the hard stop and associated locking position, retracting the device 200 will result in sliding the outer handle 202 proximally, warning the user that full deployment of the nasal implant 232 was not achieved.

Advantageously, because the user holds only the outer handle 202 of the device 200 and not the inner handle 208, the user will not place a counter load (i.e., $F_{GRIP}$ in FIG. 2D) on the inner handle 208 or needle 206. As a result, the tool 200 is not retracted relative to the tissue during deployment. Also, because the user can use the outer handle 202 as both a grasping mechanism and the plunger, the user is less likely to change hand grip or orientation during use, thereby helping to ensure that the orientation of the tool 200 and thus the implant 232 remains consistent during deployment.

Figure 4A:
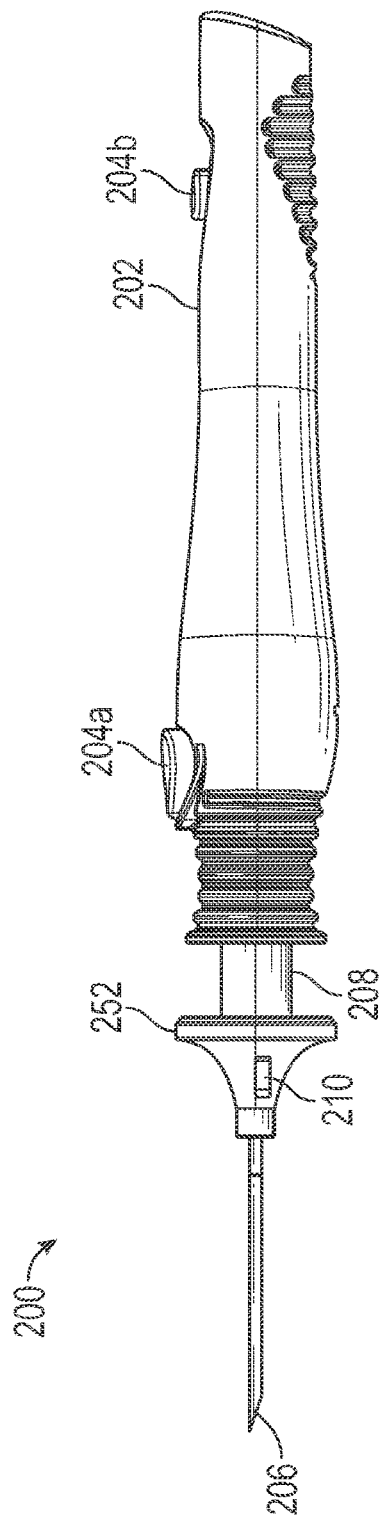
FIGS. 4A and 4B illustrate an exterior side view and a cross-sectional side view, respectively, of the delivery the delivery tool of FIGS. 3A-3C.
Figure 4B:
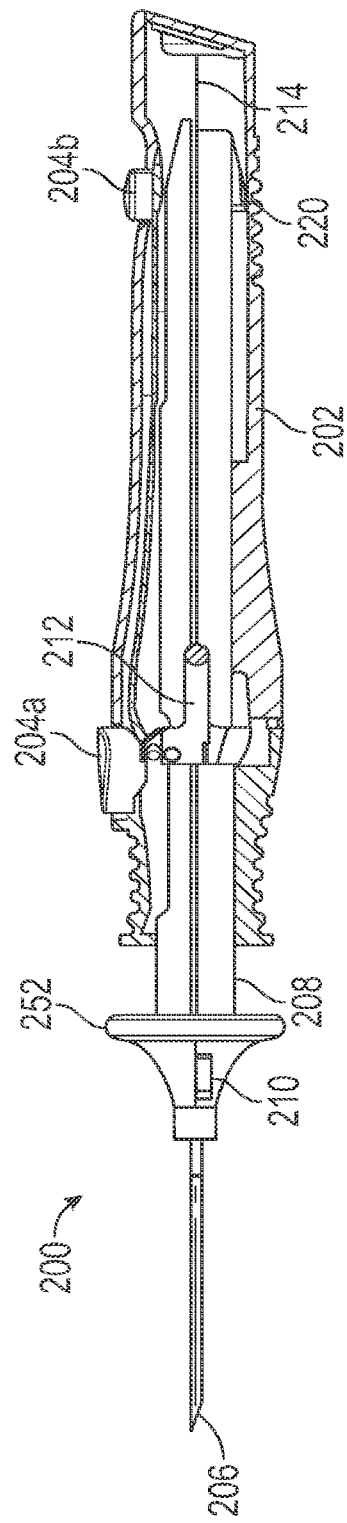
Figure 4C:
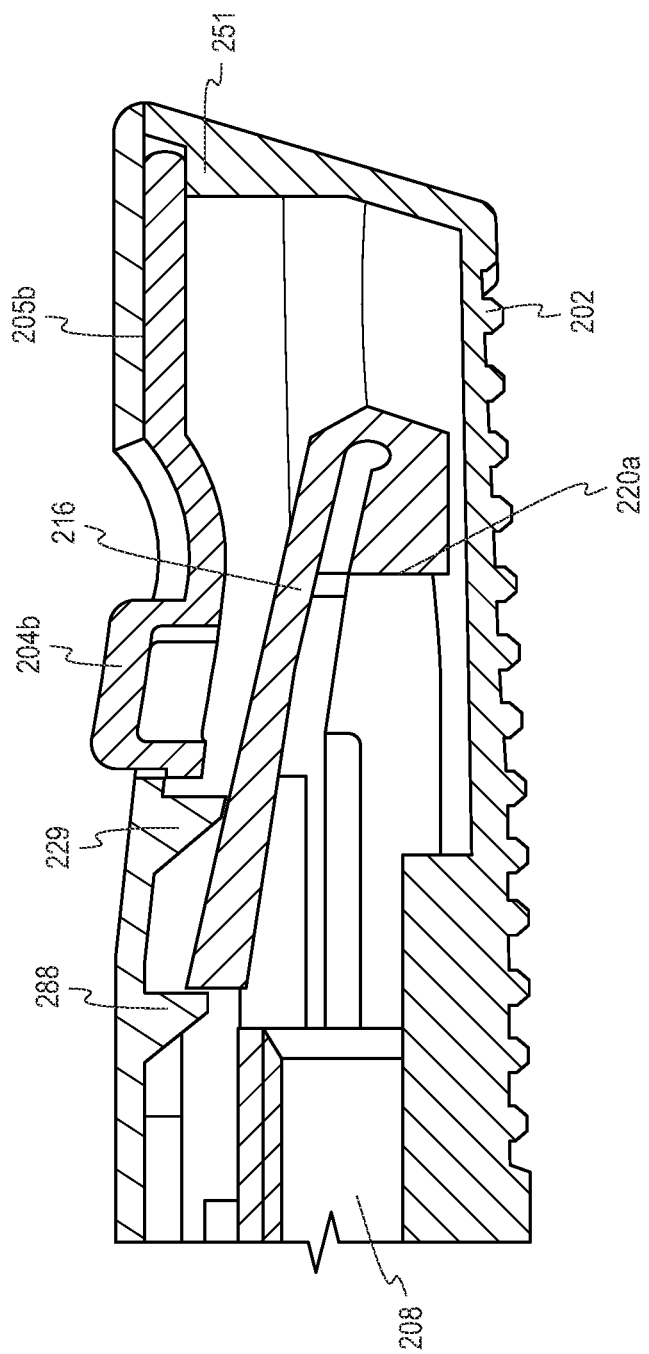
FIGS. 4C-4E show use of the proximal button to allow proximal retraction of the outer handle relative to the inner handle.
Figure 4D:
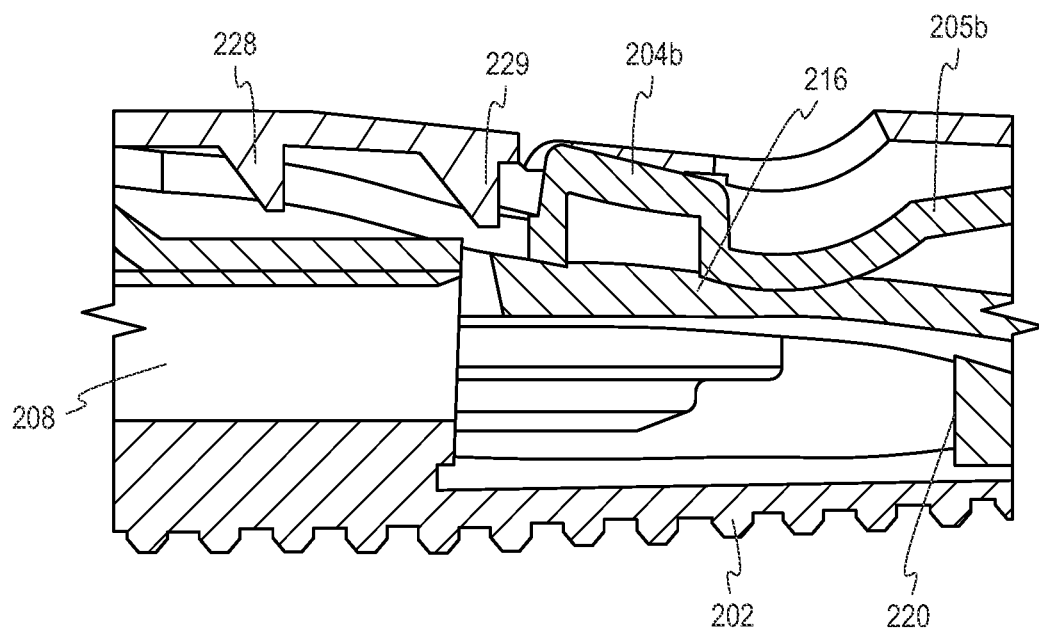
Figure 4E:
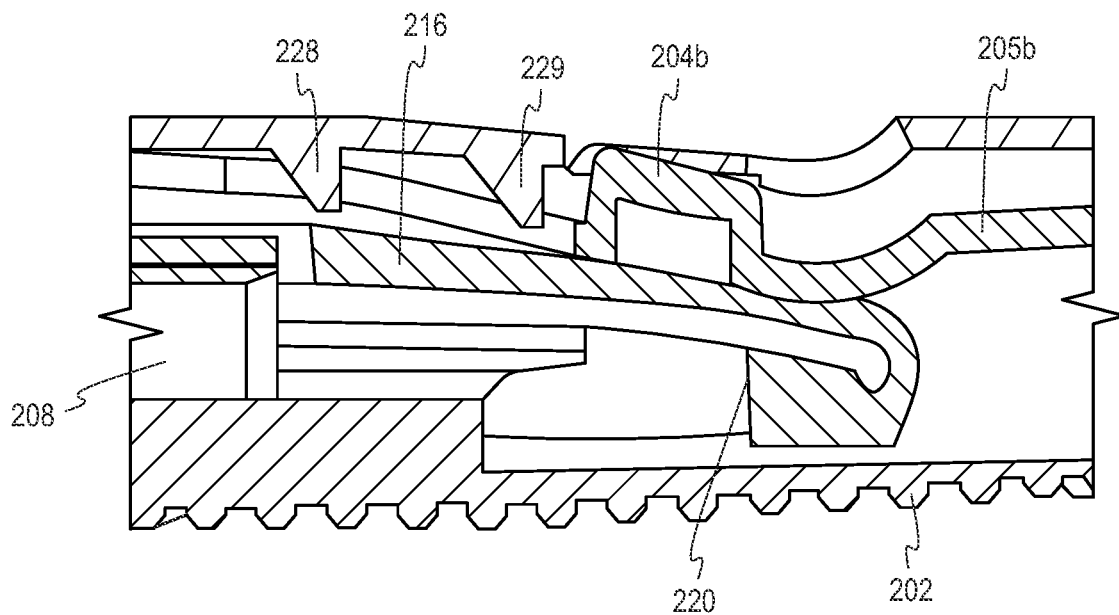

FIGS. 4A-4C show the delivery device 200 in a pre-loaded configuration (i.e., without an implant therein). The cross-sectional view in FIG. 4B shows the distal button 204a engaged with a latch 212 of the inner handle 208, as the distal button 204a has not yet been depressed. Further, in this position, the proximal button 204b is also not depressed. A cantilevered portion 205b of the proximal button 204b can have spring-like properties to bias the button 204b in the upwards direction. This cantilevered portion 205b can be heat staked or bonded to the inner surface of the outer handle 202 distal to the button and supported by a rib feature 251 proximal to the proximal button. Further, a retraction stop tang 216 on the inner handle 208 can be engaged with a distal tooth 228 on the outer handle 202. This engagement can prevent the outer handle 202 from retracting proximally relative to the inner handle 208 in the pre-loaded configuration. Referring to FIGS. 4D and 4E, to load an implant into the device 200, the proximal button 204b can be depressed to push the retraction stop tang 216 away from the distal tooth 228. As the proximal button 204b is held down, the outer handle 202 can be retracted proximally relative to the inner handle 208 and proximally past the distal tooth 228 and the proximal tooth 229 to allow for loading of the implant.

Figure 5A:
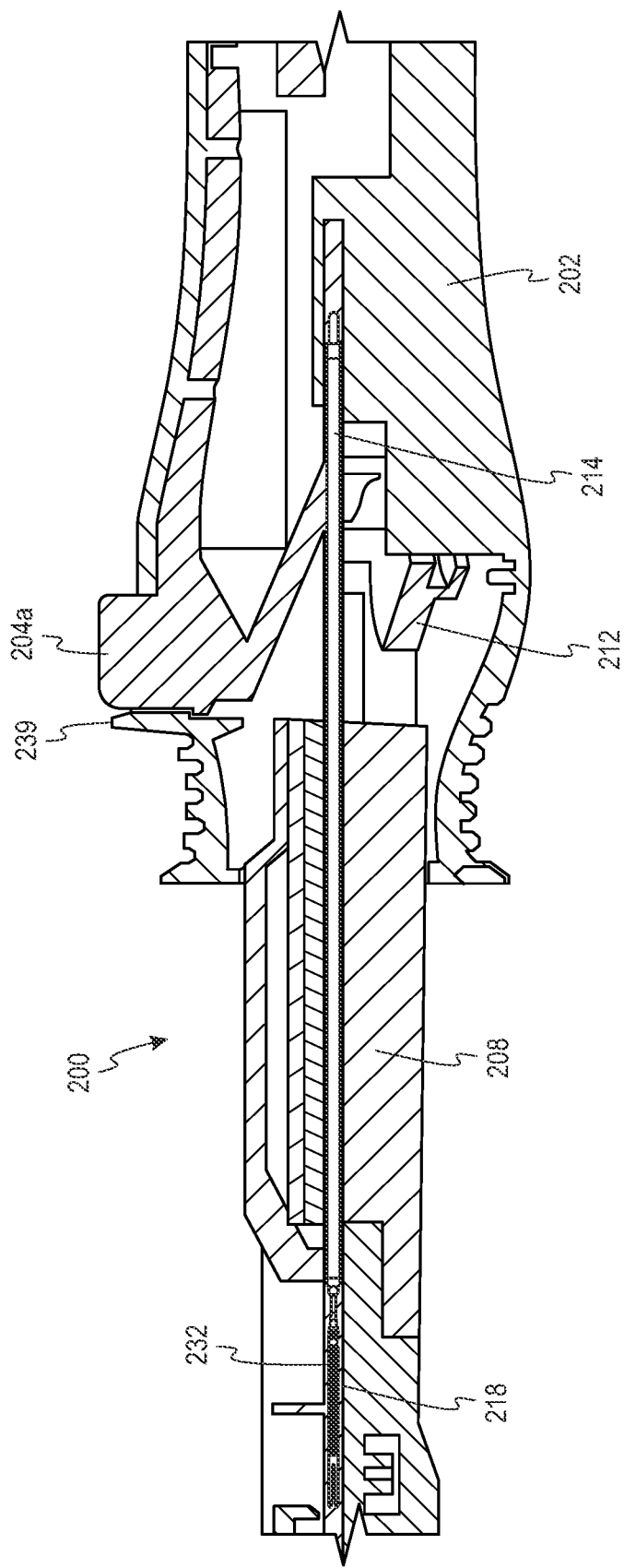
FIG. 5A illustrates a cross-sectional views of the delivery tool of FIGS. 3A-3C in an implant loading configuration.

FIGS. 5A-5E show the delivery tool 200 in a loading configuration ready for loading of an implant. The outer handle 202 has been retracted proximally relative to the inner handle 208 to expose an implant loading chamber 218. In the retracted position, the retraction stop tang 216 of the inner handle 208 can hit a stop tooth 239 and simultaneously the tang latches 220a (connected to the stop tang 216) can hit the stop rib 220b to prevent the inner handle 208 and outer handle 202 from becoming completely separated. Retraction of the outer handle 202 exposes the implant loading chamber 218 and fully pulls the internal push rod 214 proximally such that it is clear of the implant loading chamber 218 and the implant can be loaded. In one embodiment the delivery tool can be configured such that while the loading configuration, the distal button 204a can be prevented from being depressed (i.e., to prevent accidental deployment of the implant while moving the device into the ready configuration). As shown in FIG. 5D, in the loading configuration, a t-slot feature 219 on the inner surface of the latch 212 can ride along a rail 221 on the inner handle 208, thereby preventing the distal button 204a from being pushed downwards. The rail 221 can extend from only part way along the length of the inner handle 208 (e.g., 40-80%, such as 60%) and can end right at position of the t-slot feature 219 in the primed or pre-loaded configuration (thereby allowing the t-slot feature 219 to disengaged and move the button 204a back up into position).

Figure 6A:
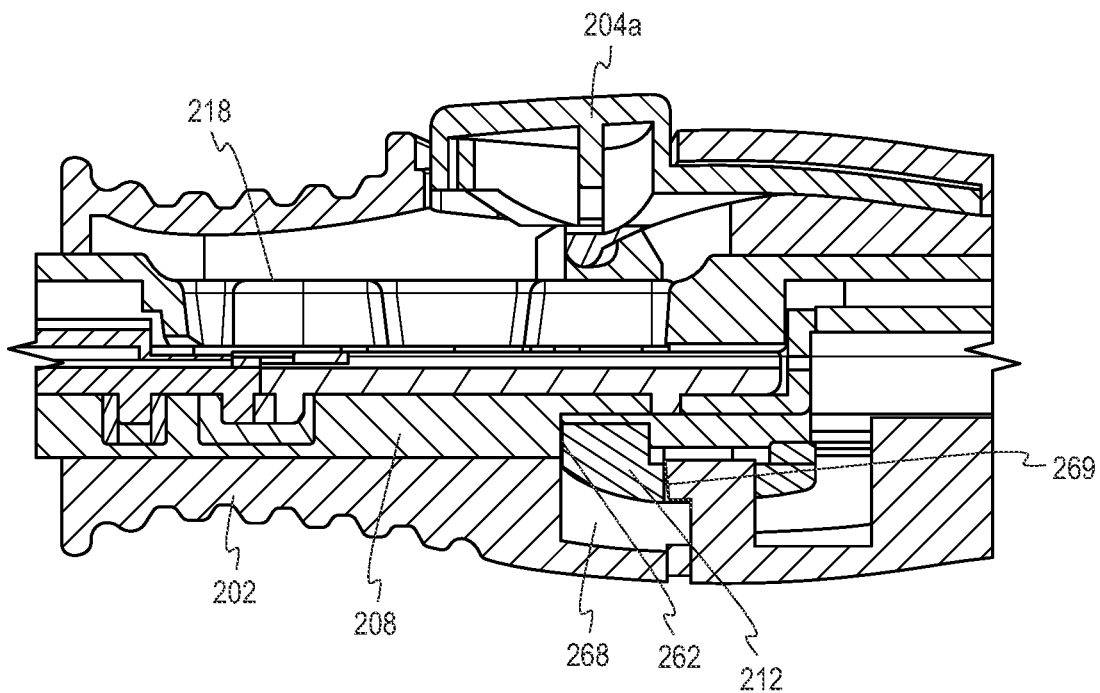
FIGS. 6A-6B illustrate the delivery tool of FIGS. 3A-3C after pressing a deployment button to deploy a nasal implant.
Figure 6B:
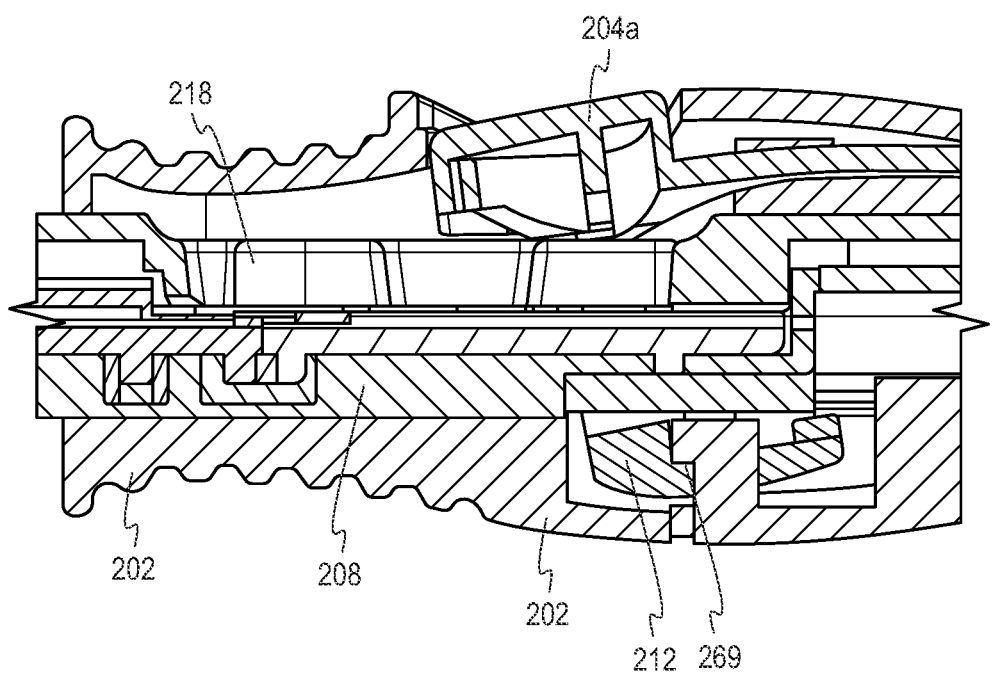

After loading the nasal implant into the loading chamber 218, the outer handle 202 can be slid distally until it reaches the ready position hard stop 262 on the inner handle 208 shown in FIG. 6A. This positions the device 200 back in the primed configuration shown in FIG. 3A. In this position, the t-slot feature 219 is disengaged from the rail 221 on the inner handle 208 with the distal button 204a, remaining in a non-depressed position. In this position, the deployment button is free to be depressed when ready for deployment. In the primed position, A user (e.g., physician) can then use the delivery tool to deliver the nasal implant to the targeted nasal tissue. The user can thus insert the needle 206 of delivery tool 200 (with the implant therein) in the primed configuration into the nasal wall of the patient. While the user is navigating the nasal wall anatomy, the device 200 can experience both tensile and compressive loads due to friction and resistance of the target tissue, but the handles 208, 202 will not move relative to one another.

Figure 6C:
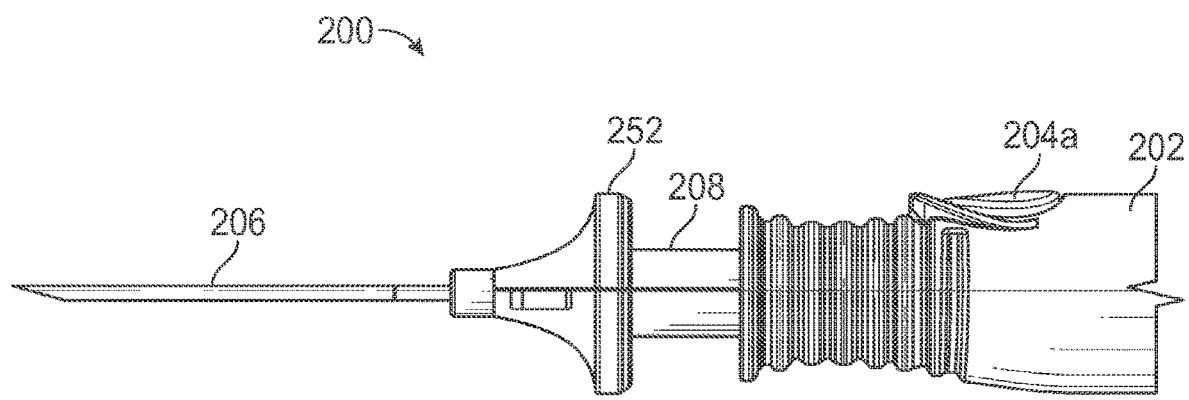
FIGS. 6C-6D illustrate the advancement of the outer handle of the delivery tool of FIGS. 3A-3C to deploy an implant.
Figure 6D:
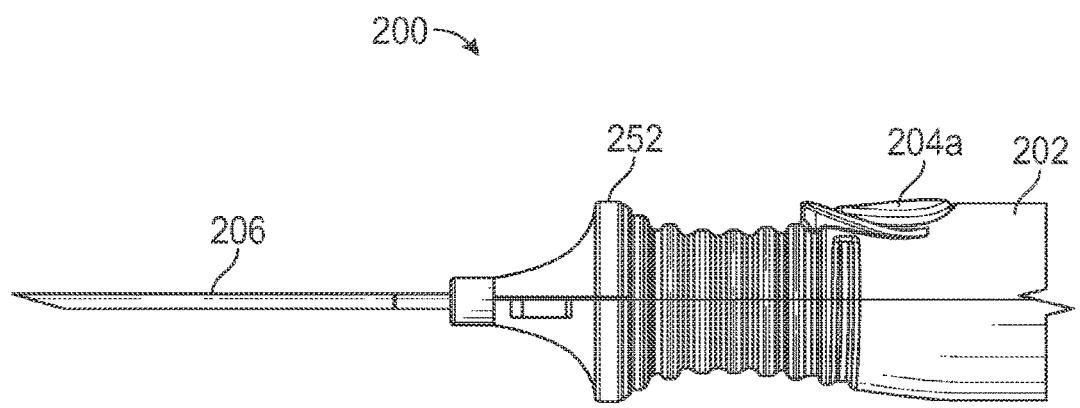

Referring to FIG. 6A-6D, once the user has positioned the device 200 in the appropriate position in the body and is ready to deploy the implant, the distal button 204a can be depressed. Upon pressing the distal button 204a, the button 204a will push the latch 212 downwards (i.e., into the clearance space 268), causing it to catch under the lip 269 of the outer handle 202 (as shown in the change from FIG. 6A to FIG. 6B). In some embodiments, this activation can create an audible and/or tactile feedback mechanism to provide indication to the user that the implant is ready to be deployed (i.e., that the deployment lock has been released). Once latched, the user can release the distal button 204a (though release of the button is not required), as the distal button 204a will remain depressed (due to the latch 212 being caught on the lip 269). After pressing the distal button 204a, the user can slide the outer handle 202 forward (as the latch 212 is no longer engaged with the lip 262 on the inner handle 108), as shown in the change from FIGS. 6C to 6D. As the outer handle 202 moves forward, the push rod 214 moves distally to push the implant from the loading chamber 218 and deploy the implant. As shown in FIGS. 6C-6D, the user can advance the outer handle 202 forward until the outer handle 202 reaches a hard stop against the flange 252.

Figure 7A:
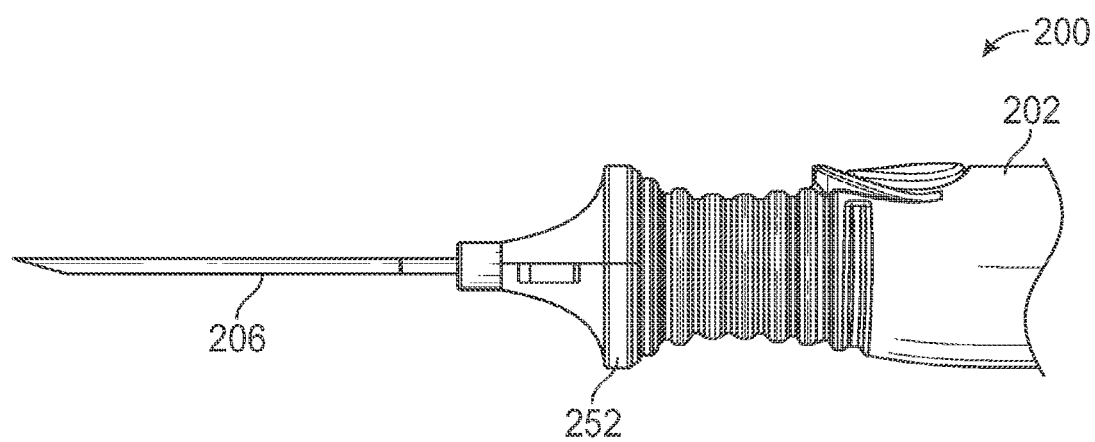
FIG. 7A illustrates the position of the outer handle of the delivery tool of FIGS. 3A-3C after delivery of the implant.
Figure 7B:
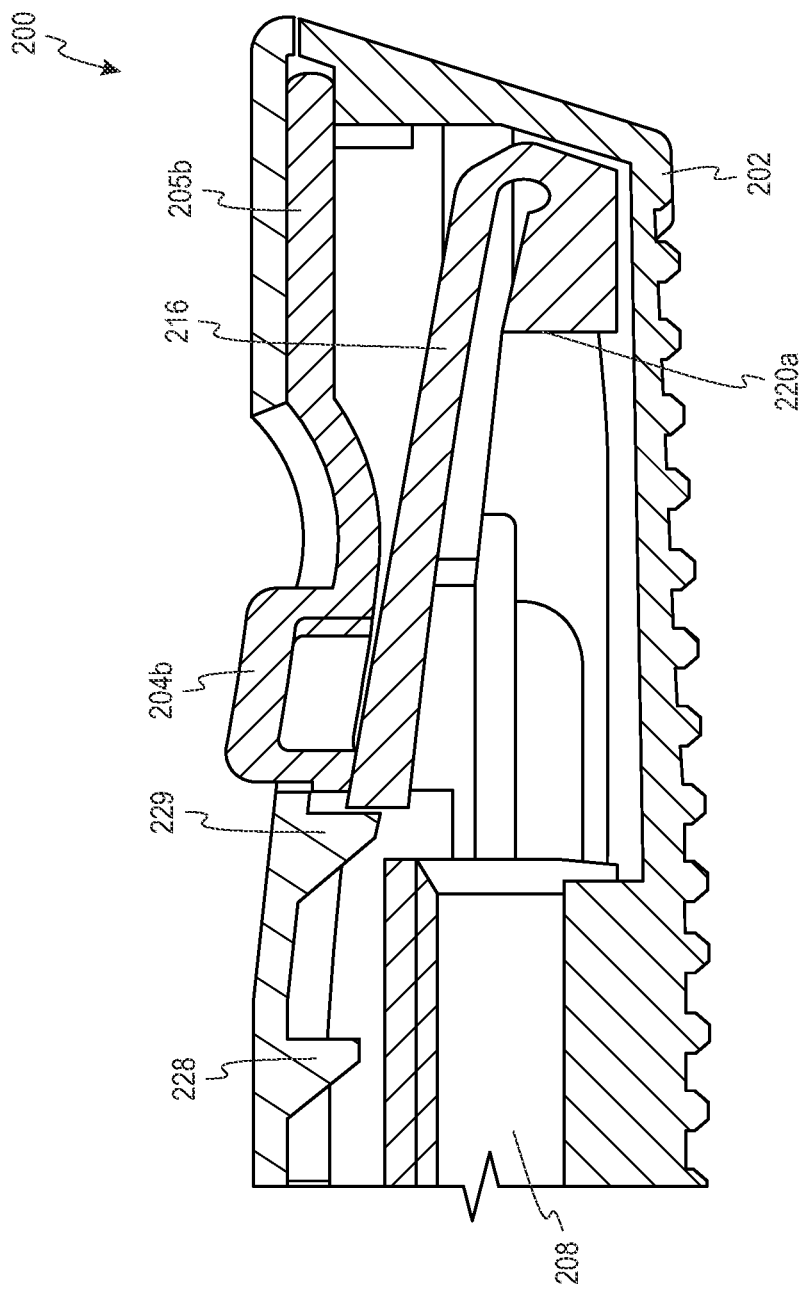
FIG. 7B illustrates a portion of the handle of the delivery tool of FIGS. 3A-3C that includes a retraction lock.

As shown in FIGS. 7A-7B, once the outer handle 202 has reached the hard stop against the flange 252, the handle 202 can lock into place to allow retraction of the device 200. Referring to FIG. 7B, in this position, the retraction stop tang 216 can move proximal to the proximal stop tooth 229 such that the tang 216 rests against the proximal tooth 229, thus preventing the outer handle 202 from moving proximally relative to the inner handle 208. This lock allows for the physician to retract the device 200 from the soft tissue without unsheathing the outer handle 202 from the inner handle 208. This latching action can create an audible and/or tactile feedback mechanism to provide indication that the implant has been fully deployed or fully released and that the device is latched in the deployment position (i.e., prior to full release, the outer handle 202 can be moved proximally relative to the inner handle 208 thus indicating that the implant has not been properly or fully released).

Figure 8A:
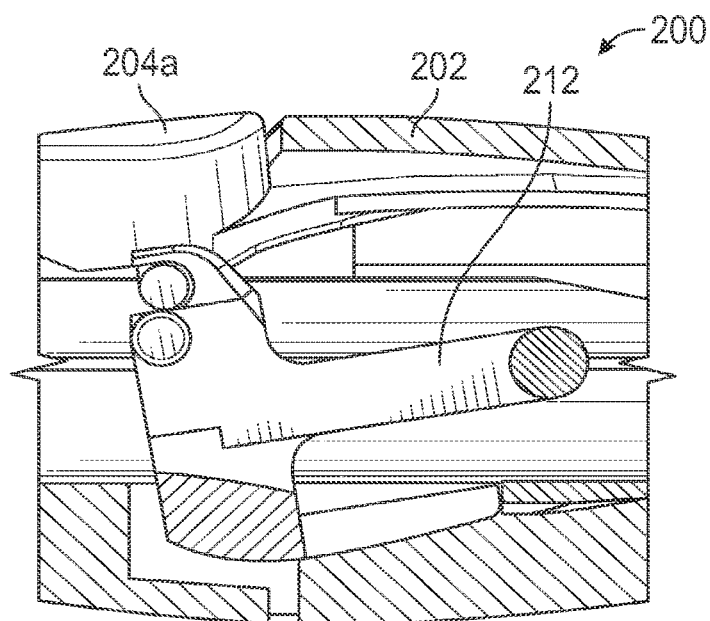
FIGS. 8A-8C shows a portion of a handle of the delivery tool of FIGS. 3A-3C to illustrate the operation of the deployment button, inner latch mechanism, and reset mechanism.
Figure 8B:
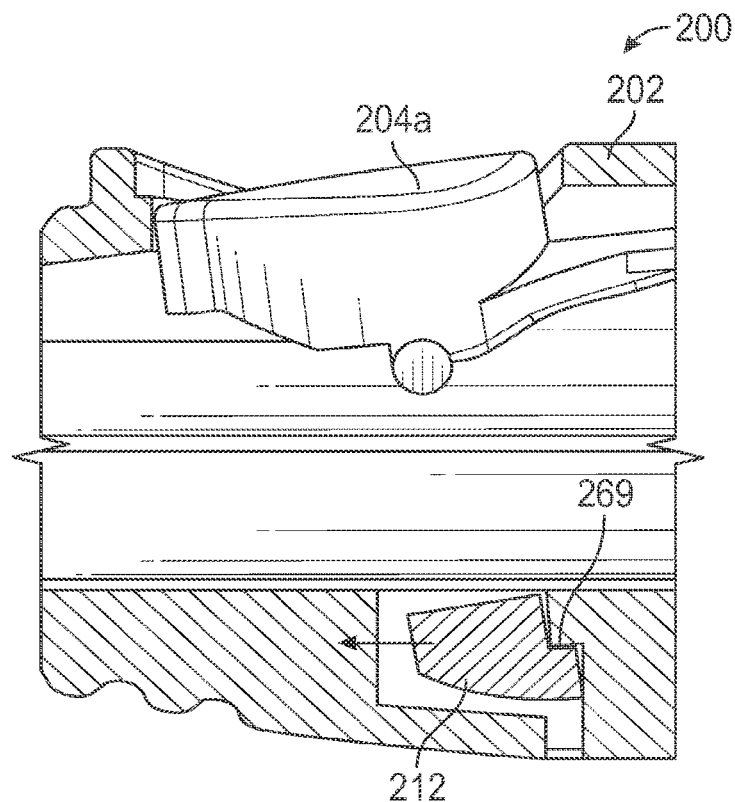
Figure 8C:
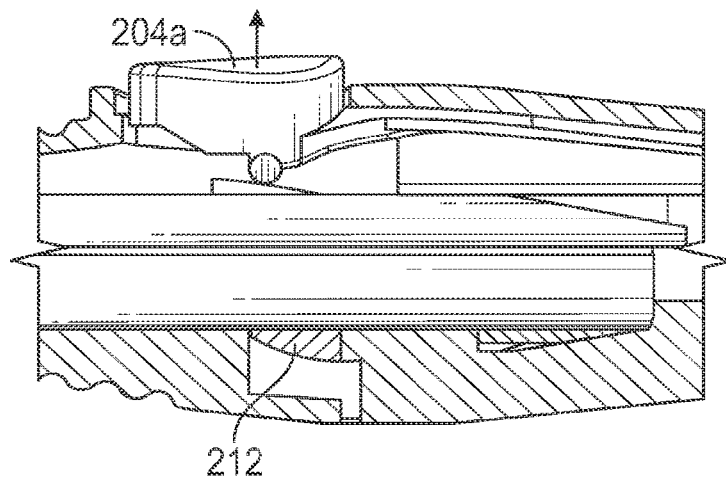

After delivering the nasal implant, the device 200 can be reloaded with another implant by pushing the button 204a as described above with respect to FIGS. 4A-4D. Further, referring to FIGS. 8A-8C, as the outer handle 202 is pulled proximally, the deployment button 204a engages with the proximal edge of the implant loading chamber 218 which pushes latch 212 out of engagement with the lip 269, allowing the latch 212 and the button 204a to spring upwards (e.g., the button 204a and/or latch 212 can be spring biased towards the upwards position to cause the button 204a to move upwards as shown in the change from FIGS. 8B to 8C).

Figure 9A:
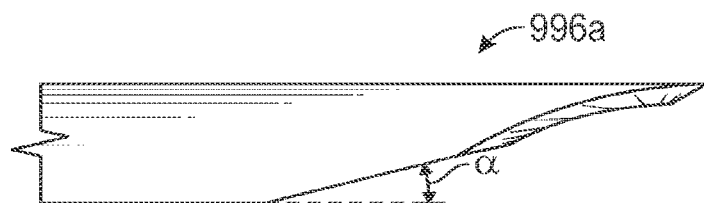
FIGS. 9A-9B show different views of an exemplary tip of a needle of a delivery tool.
Figure 9B:
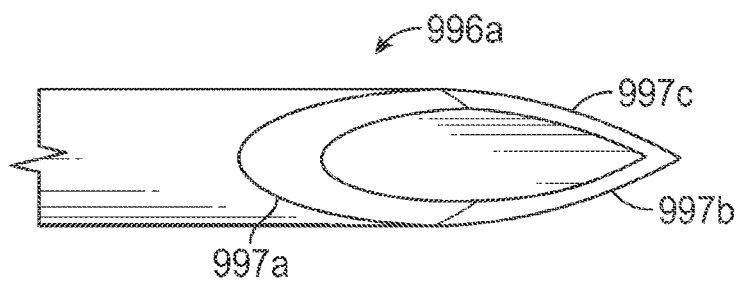
Figure 9C:
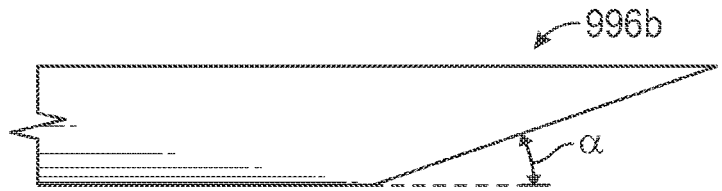
FIGS. 9C-9D show different views of another exemplary tip of a needle of a delivery tool.
Figure 9D:
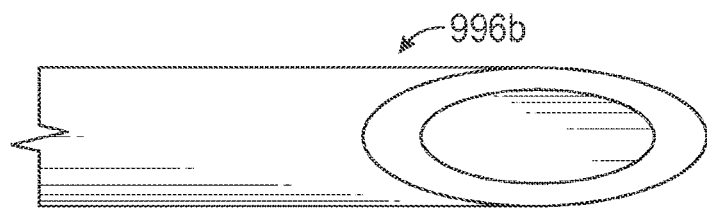
Figure 9E:
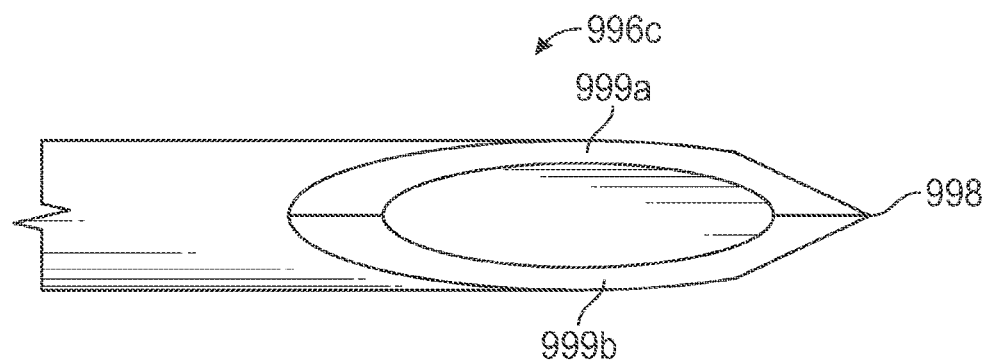
FIGS. 9E-9F show different views of another exemplary tip of a needle of a delivery tool.
Figure 9F:
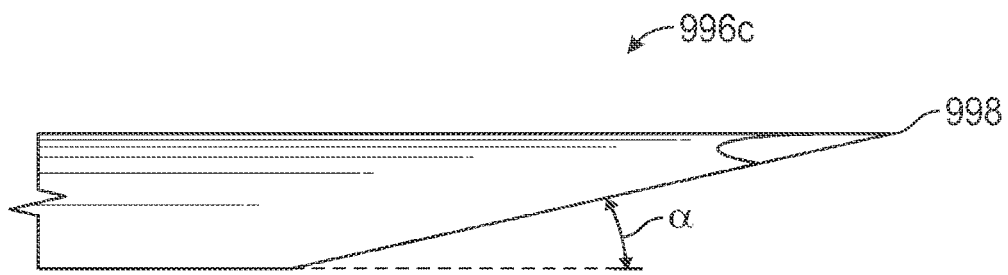

Referring to FIGS. 9A-9F, the tip of needle (e.g., the needle 206 of device 200) can be used to facilitate penetration of tissue and/or tissue separation during positioning of the delivery needle 206 for delivery of the nasal implant 232. For example, referring to FIGS. 9A-9B, a tip 996a can have a tri-bevel faceted configuration that includes three distinct surfaces 997a-c, each of which is beveled (i.e., beveled at 45 degrees from the primary bevel orthogonal plane). Further, the tip 996a can have a primary angle α that varies from about 11-15 degrees. As another example, referring to FIGS. 9C-9D, a tip 996b can have a flat bevel design without a faceted tip. The tip 996b can have a primary angle α of between 15-20 degrees. The flat beveled tip 996b can have less of a cutting tip (e.g., than tip 996a) that can enable one or more of the following: tissue layer differentiation for improved plane detection (i.e. Dermis, Upper and Lower Lateral Cartilages, Mucosa), differentiation between forces encountered in the different tissue types, and a reduction in cannula travel vector bias to improve soft tissue plane dissection. Referring to FIGS. 9E-9F, a tip 996c can have two beveled surfaces 999a,b (e.g. beveled at 45 degrees) that meet in a sharp pointed end 998. The tip 996c can have a can have a primary angle α of between 11-20 degrees. The beveled configuration of tips 996a, 996b, and 996c can facilitate easier access to the mid-thickness plane of the nasal valve wall. The beveled design of tips 996a, 996b, and 996c can also result in a heightened resistance to cephalic travel when positioned over the maxilla for implant deployment. The bevel grind angles can balance strength of the tip geometry, tip sharpness, and affects the interaction of the implant arms (forks) during soft tissue engagement.

A number of alternatives can be used in the delivery tools described herein, such as for the buttons on the handle and hard stops and locking structures in the inner handle portion of the delivery tool.

Figure 10A:
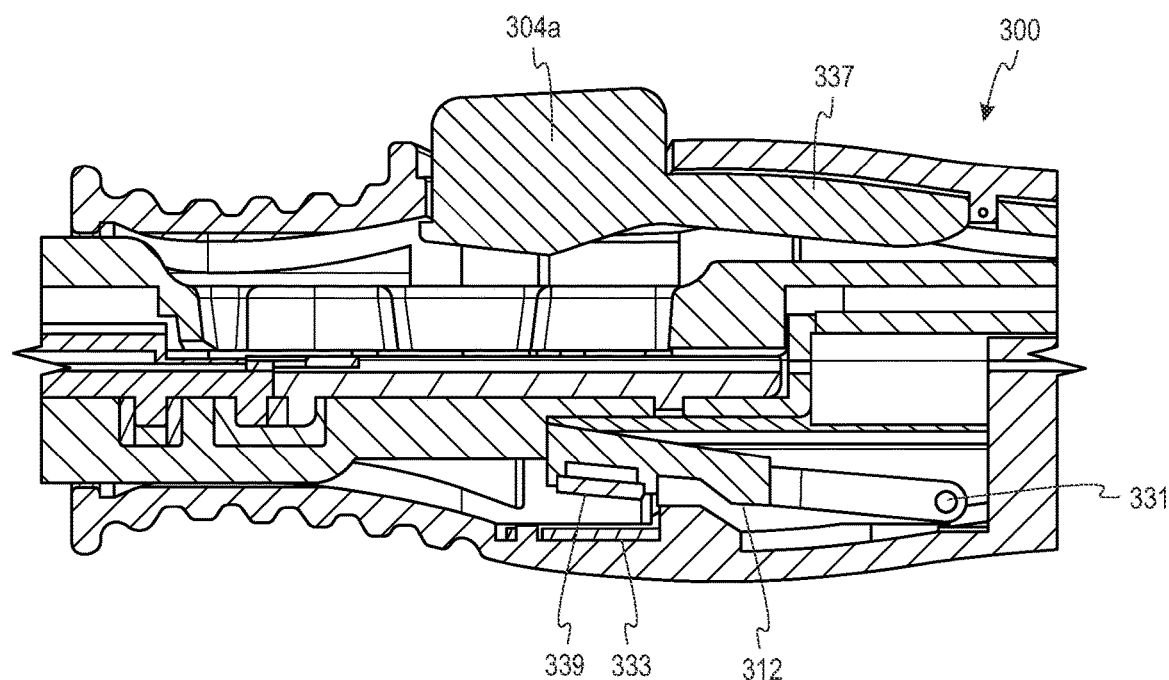
FIGS. 10A-10C illustrate a portion of a handle of another exemplary delivery tool.
Figure 10B:
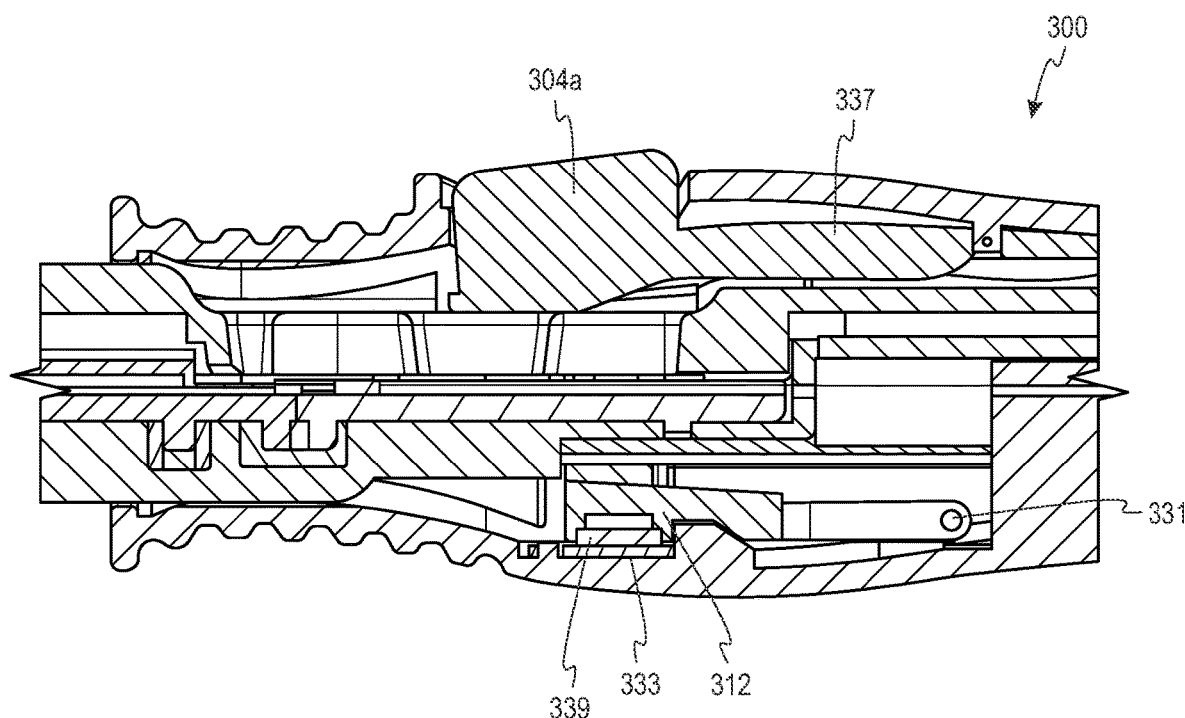
Figure 10C:
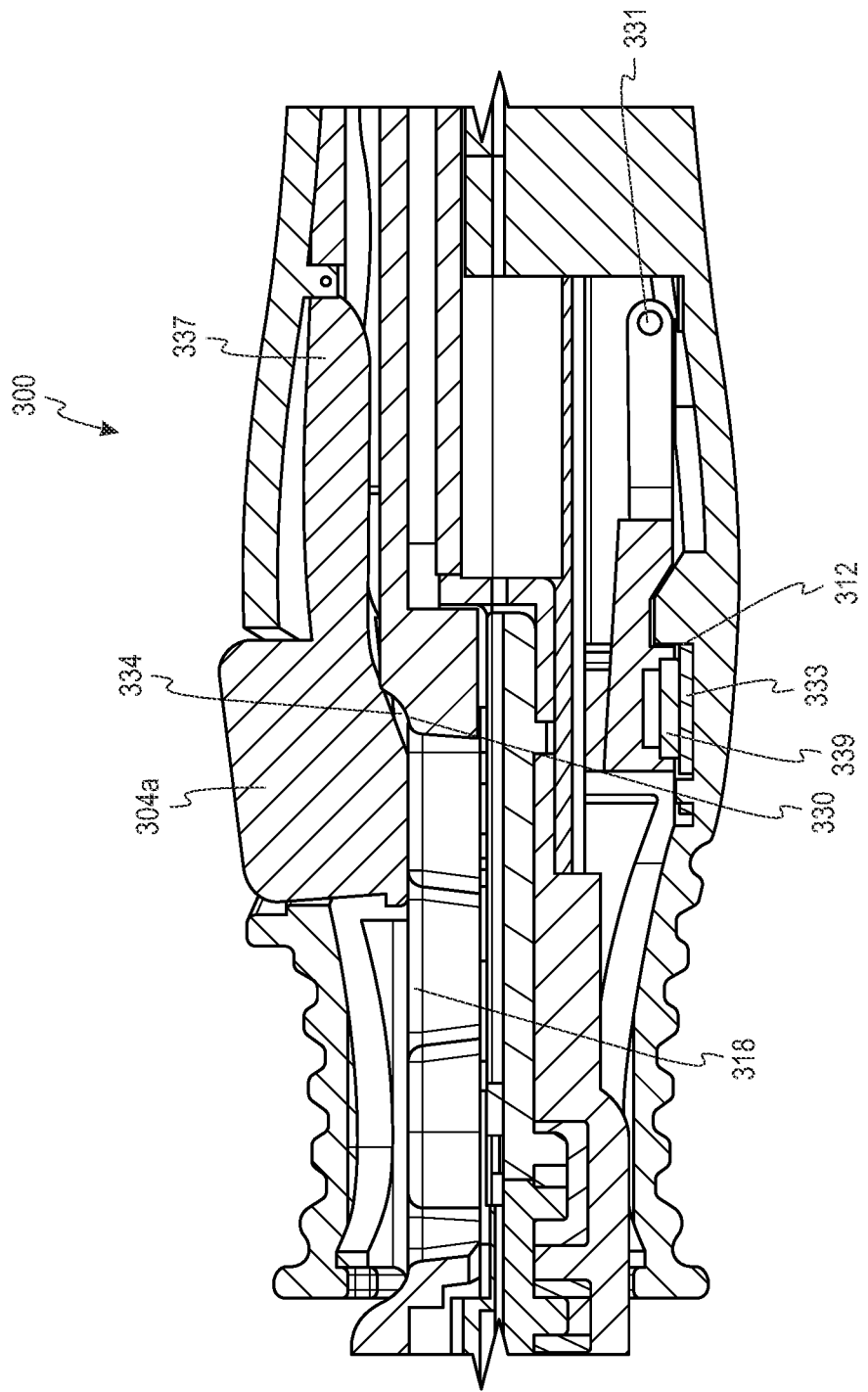

In some embodiments, a button with a magnetic latching design can be used. FIGS. 10A-10C illustrate a portion of a handle of an exemplary delivery tool 300. The delivery tool 300 is similar to delivery tool 200 except that the distal button 304a can be attached to a latch 312 that attaches to a magnetic stop 333 when depressed. The button 304a can include a living spring 337 that biases the button 304a upwards. When depressed (as shown in the change from FIG. 10A to 10B), the button 304a can push on the latch 312, which pivots about pivot point 331. A magnet 339 on the underside of the latch 312 can be attracted to the magnetic stop 333. The latch 312 can thus be moved out of the way to allow for deployment, as described for delivery tool 200. As shown in FIG. 10C, when the outer handle 302 is retracted, the proximal edge 330 of the implant loading port 318 can interact with a reset ramp boss 334 to pull the magnet 339 up and off of the stop 333, causing the button 304a to spring back upwards.

Figure 11A:
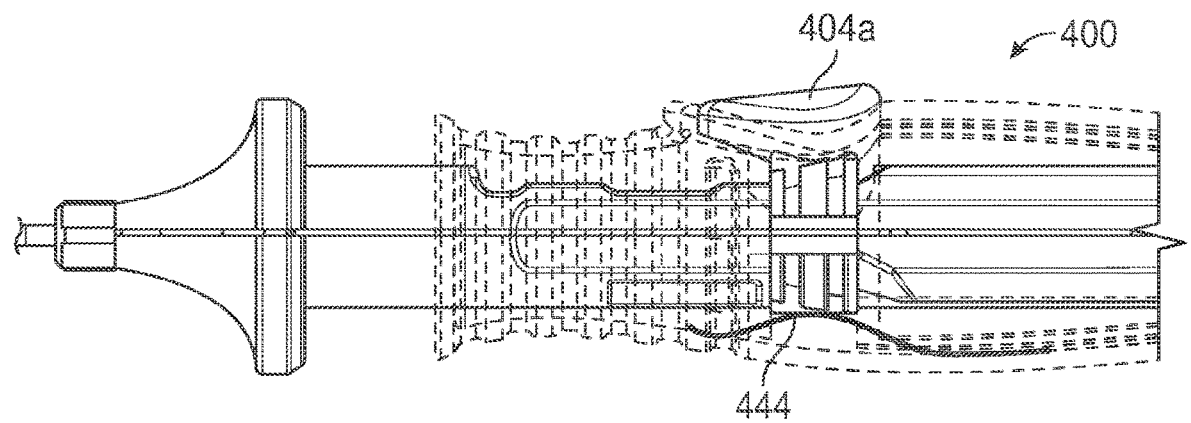
FIGS. 11A and 11B illustrate a portion of another exemplary delivery tool.
Figure 11B:
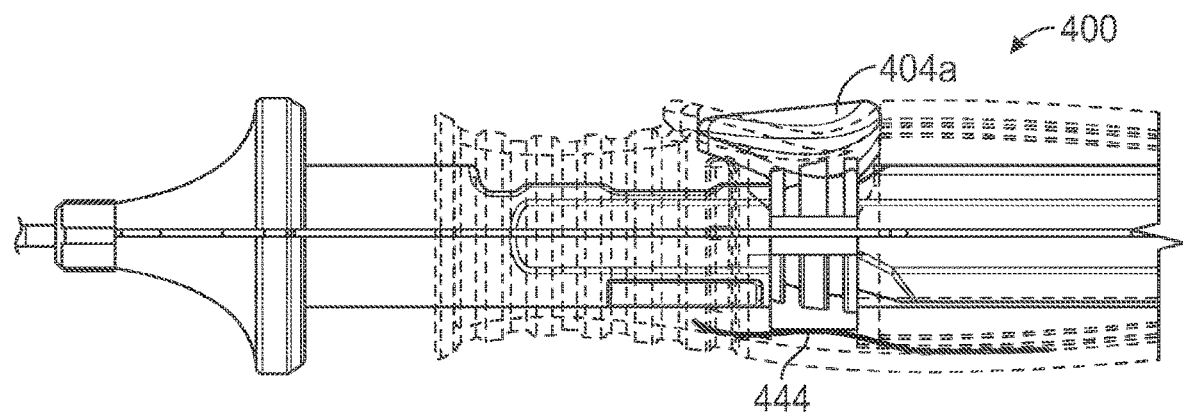

In some embodiments, a spring can be used in one or more of the locking mechanisms of the delivery tool. FIGS. 11A and 11B illustrate a delivery tool 400 that is similar to device 200 except that it includes a spring locking mechanism that can engage with and reset the distal button 404a. A spring 444 (such as a leaf spring) biases the button 404a in the upwards position. The spring 444 thus flattens as the button 404a is depressed (as shown in the change from FIG. 11A to 11B). In this embodiment, the button 404a is held in the depressed state by the user during deployment rather than latching in the depressed state. During the proximal retraction, the distal button 404a is reset with the spring 444.

Figure 12A:
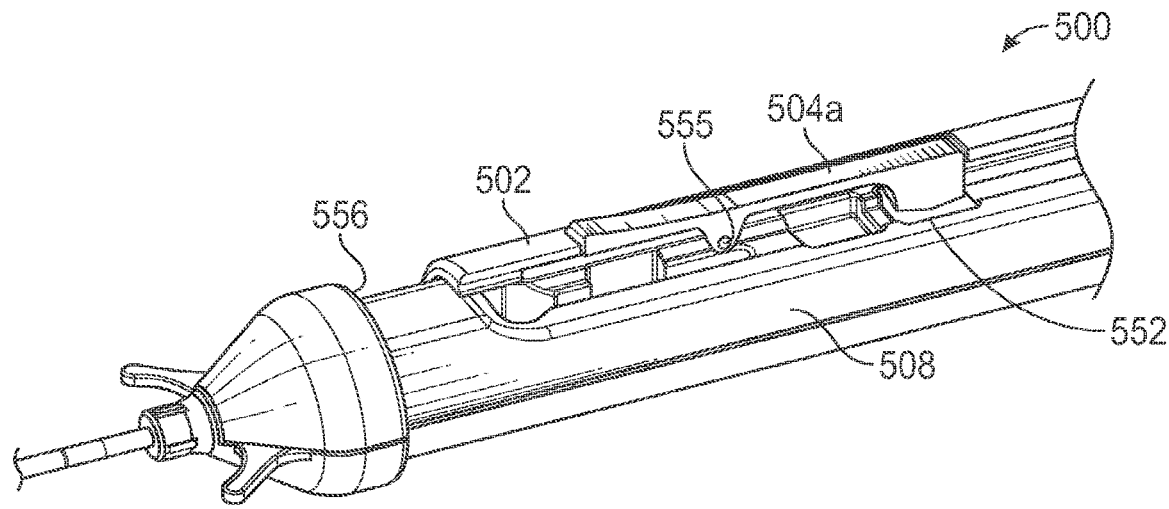
FIGS. 12A and 12B illustrate a portion of another exemplary delivery tool. A portion of the outer handle has been shown as cut away for clarity.
Figure 12B:
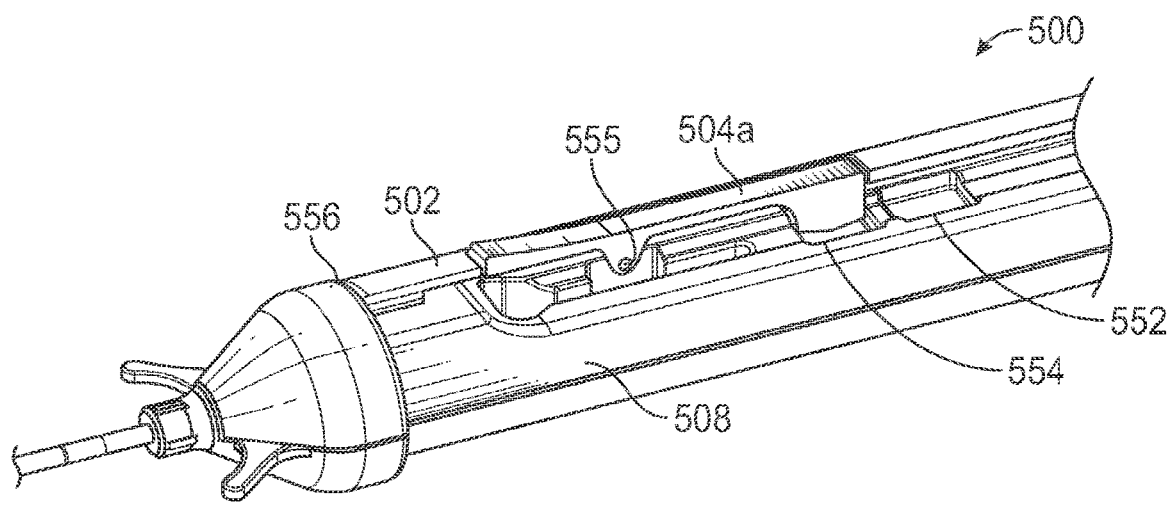

In some embodiments, the button and latch can be combined on the external portion of the delivery device. For example, FIGS. 12A-12B show a device 500 that is similar to device 200 except that the distal button 504a can be a spring-loaded latch with a central pivot point 555. A small spring (e.g., a die stamped spring) can bias the button 504a in the up position. During deployment, the user can hold the button 504a down. The latch can be configured to be positioned in a primed position (FIG. 12A) or a deployed position (FIG. 12B). From the primed position, the user can press and hold the distal (raised) portion) the lever 555 to release it from its proximal locked position 552 on the inner handle 508. The outer handle 502 can then be moved distally until the lever 555 reaches the locked position 554 on the inner handle 508 (as shown in FIG. 5B). In this position, the implant can be deployed.

Figure 13A:
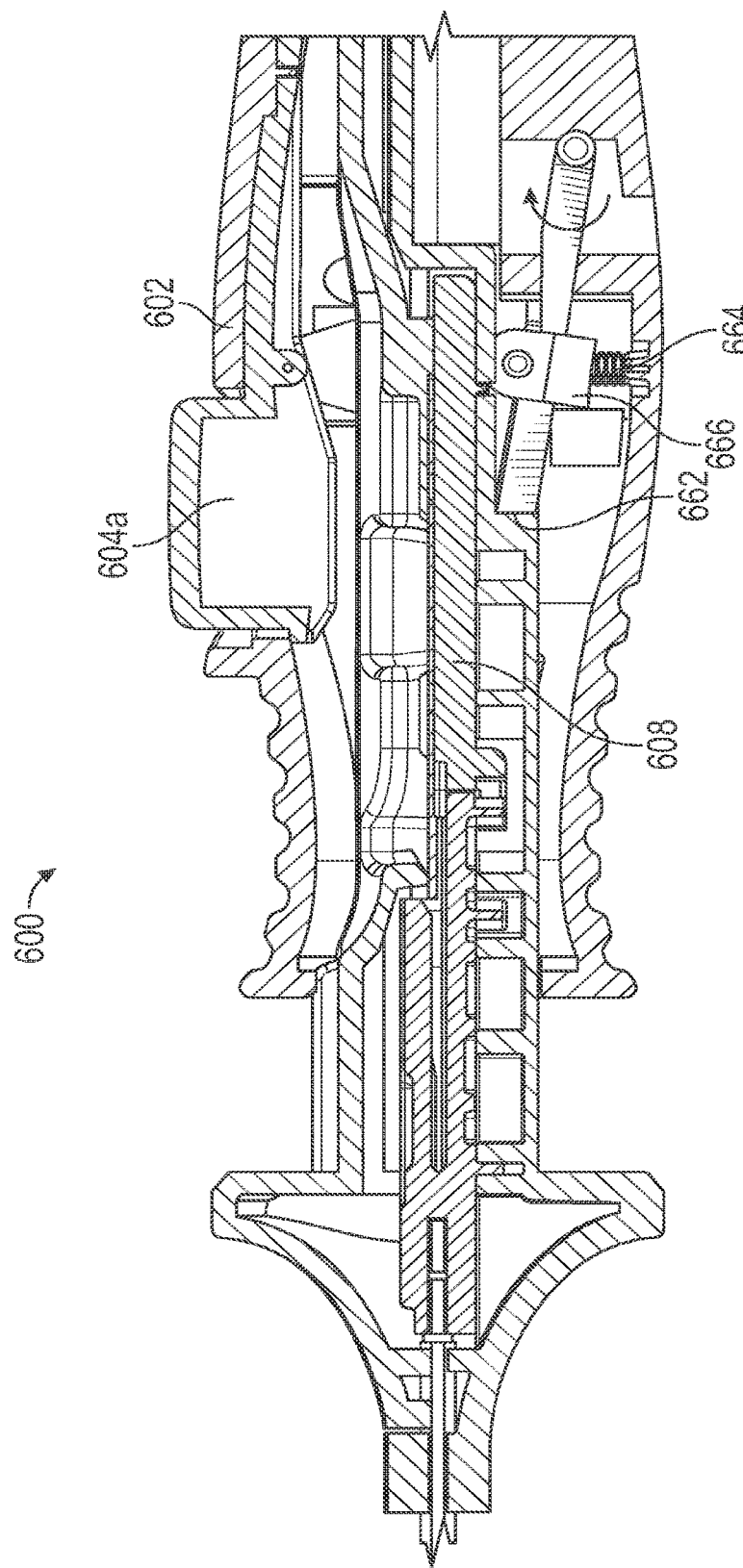
Figure 13B:
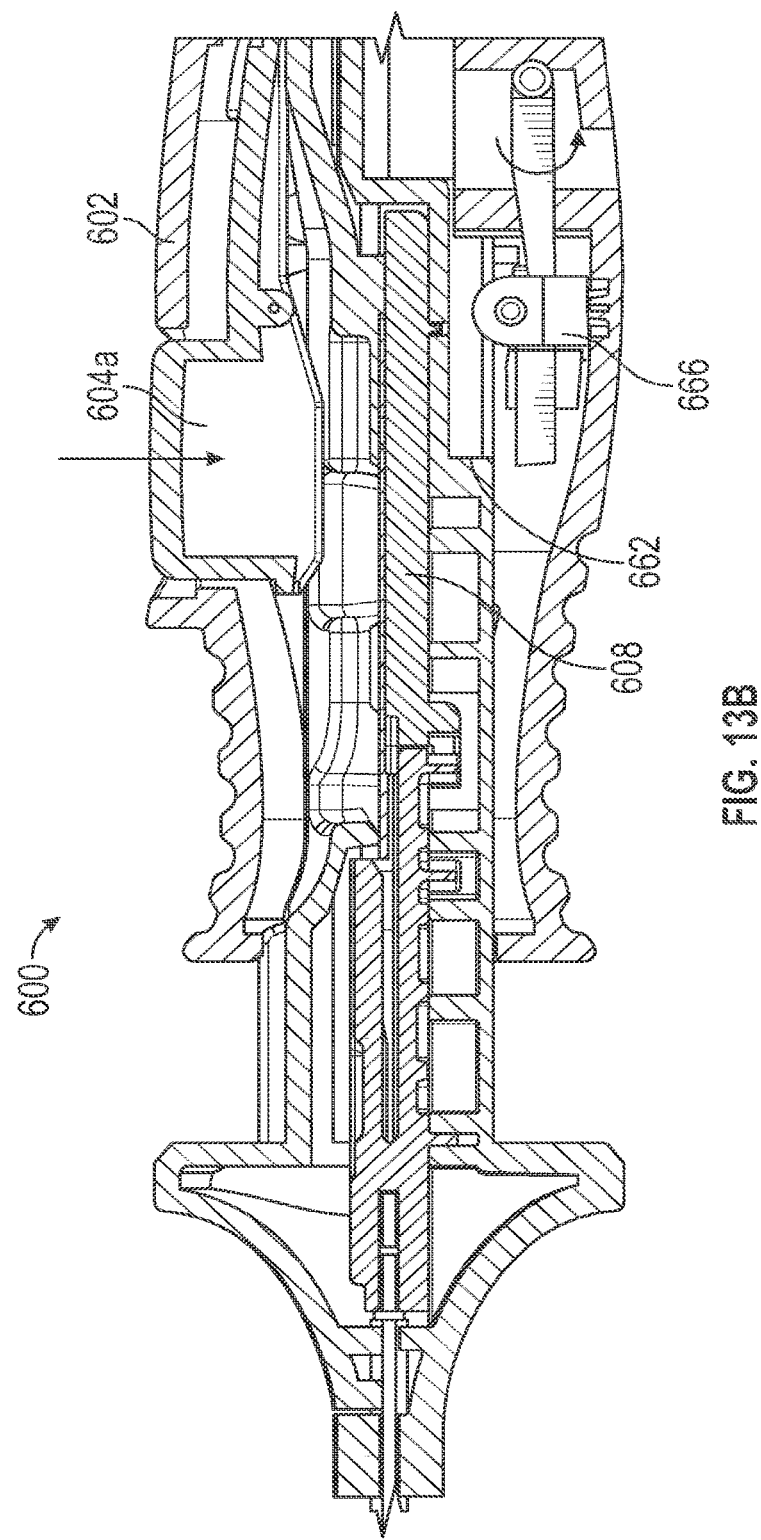
Figure 13D:
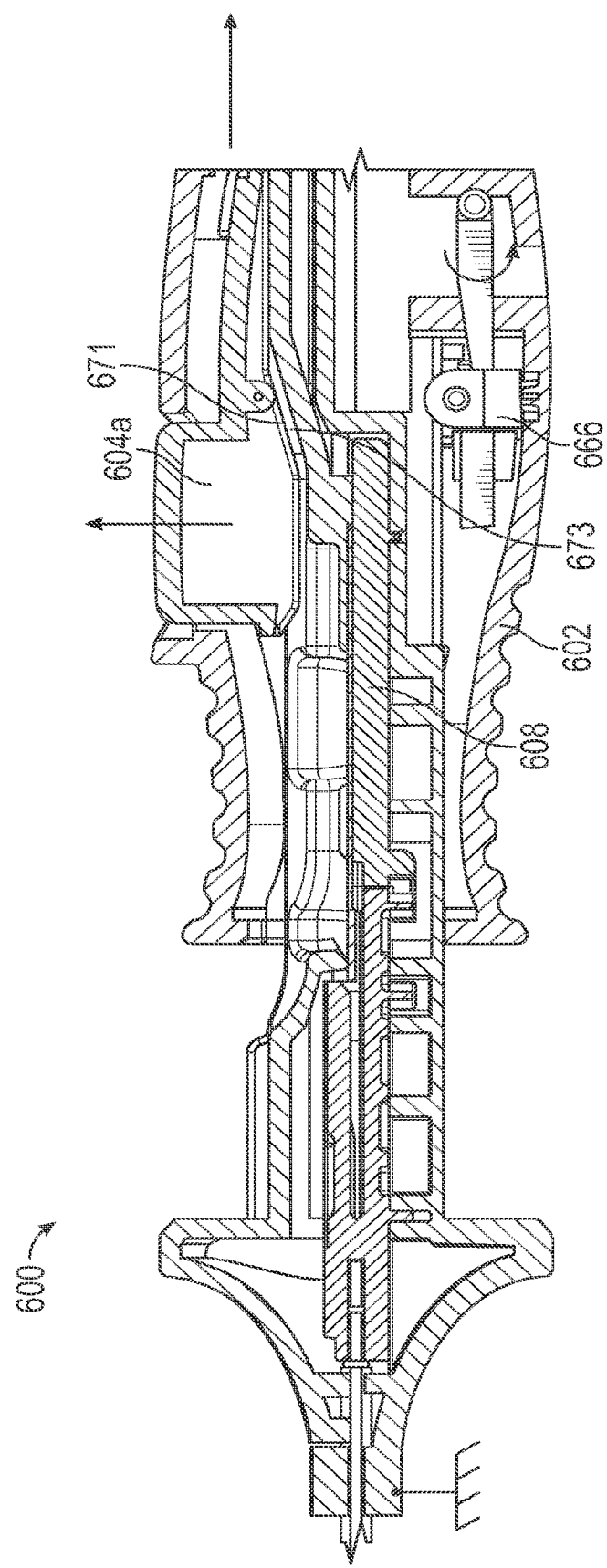

In some embodiments, a button with a spring and snap-in detent can be used. FIGS. 13A-13D illustrate a delivery device 600 that is similar to device 200 except that the distal button 604a includes a spring and snap-in detent insert. FIG. 13A shows the device 600 in the primed position. In this position, the distal button 604a is in the "up" position and the button latch 666 is also in the "up" position abutted to the hard stop 662 on the inner handle. In the prime configuration, a spring 664 holds up the button latch 666 and, similar to device 200, a retraction stop tang can be locked to prevent retraction of the outer handle 602 relative to the inner handle 208. FIG. 13B shows that as the button 604a is depressed, the button latch 666 is forced downward against the spring 664, compressing the spring 664 and clearing the button latch 666 from the hard stop 662 on the inner handle 608. In some embodiments, the button 604a can emit a click sound and/or provide a tactile response. Exemplary mechanisms that can generate the click and retain the button from springing back upwards following release is detailed in FIGS. 14A-14D, described further below. The outer handle 602 can then be advanced distally over the handle 208 for deployment of the implant. FIG. 13C shows the final deployment state of the device 600. The outer handle 602 bottoms out on the flange 652 of the inner handle 608. In this position, the retraction stop tang on the inner handle springs into a second lock position on the proximal end of the outer handle, as described above with respect to device 200. FIG. 13D shows the button 604a reset mechanism. To reload the device, the user holds down the retraction button as described above with respect to tool 200. While retracting the outer handle 602 relative to the inner handle 608, a loading port ramp 673 is designed to engage with the central rib 671 on the deployment button 604a. The ramped design of these two features 673, 671 pushes up on the distal button 604a to overcome the detent holding it down (as described with respect to FIGS. 14A-D below) and the deployment button 604a and button latch 666 spring upwards.

Figure 14A:
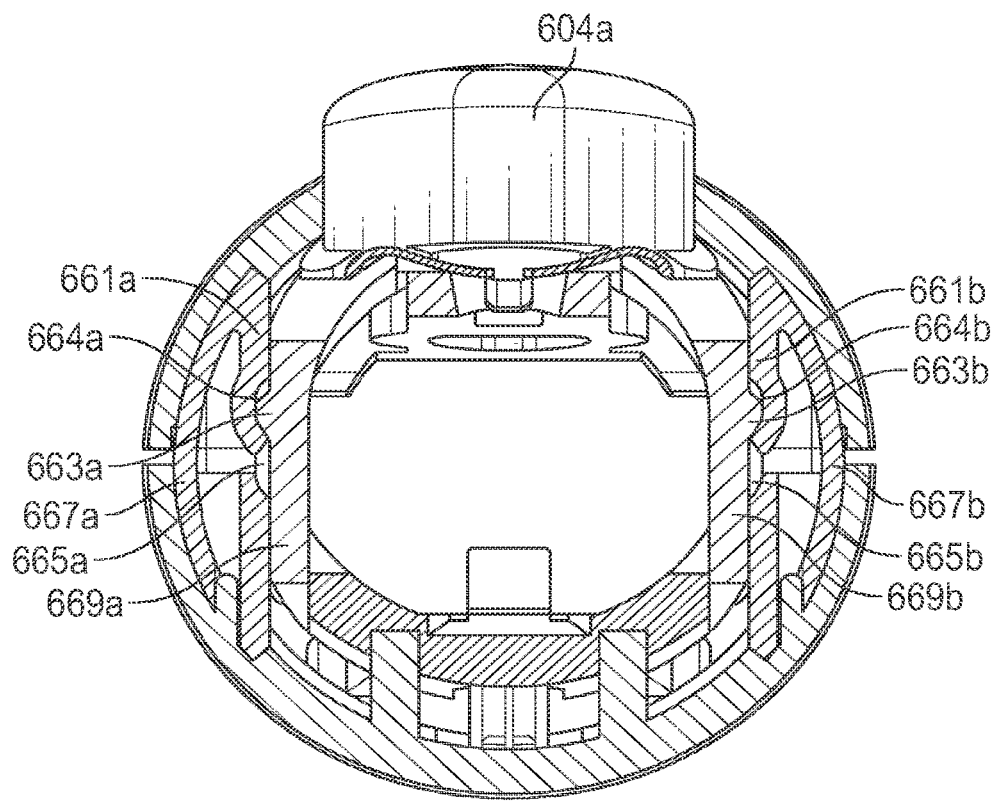
FIGS. 14A and 14B illustrate cross-sectional views of a delivery tool similar to the delivery tool of FIGS. 13A-13D.
Figure 14B:
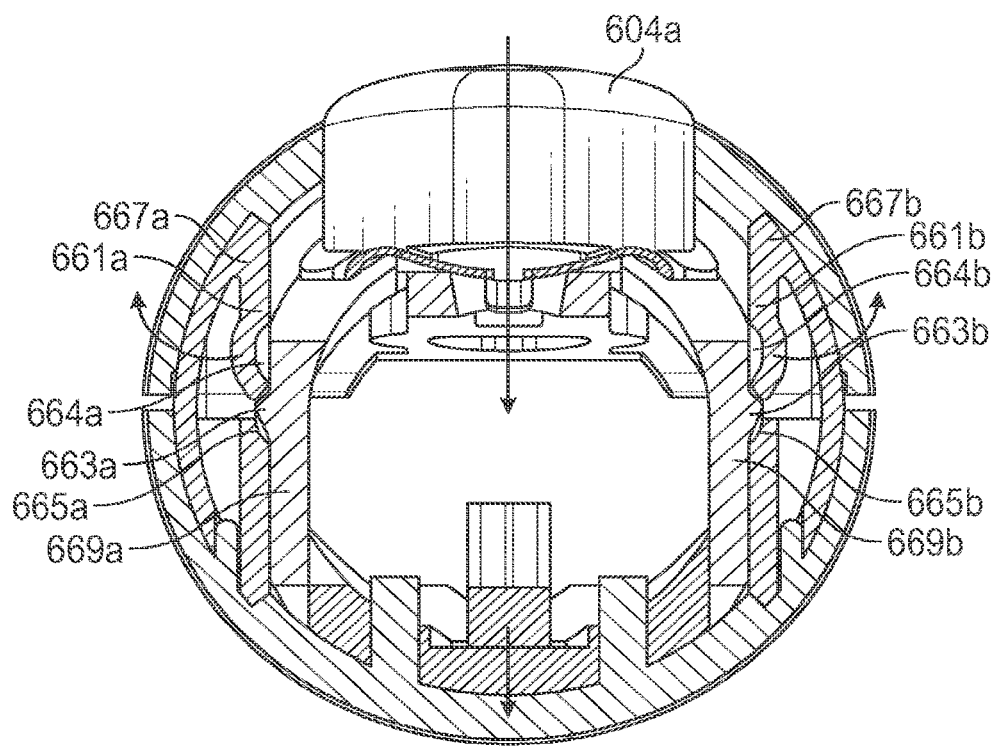

As shown in FIGS. 14A-14B, one exemplary embodiment, the button 604a can include bilateral connective linkages that engage with discrete positions on bilateral button detent inserts. FIG. 14A shows exemplary cross-sections of the device 600 through the button 604a when the button 604a is in the primed (up) position. In this position, detent bumps 663a,b on the deployment button arms 669a,b can be positioned within first reliefs 664a,b on detent insert tabs 667a,b to prevent any component preloads during shelf life. Referring to FIG. 14B, when the button 604a is depressed, the detent bumps 663a,b on the deployment button arms 669a,b can force the cantilever arms 661a,b on the detent insert tabs 667a,b to deflect out of the way (shown by the arrows in FIG. 14B) and snap back into position once the detent bumps reach a second relief 665a,b location. By snapping back into position, an audible click and/or tactile response can occur, and the detent insert tabs 667a,b can retain the button 604a in the down/depressed position.

Figure 14D:
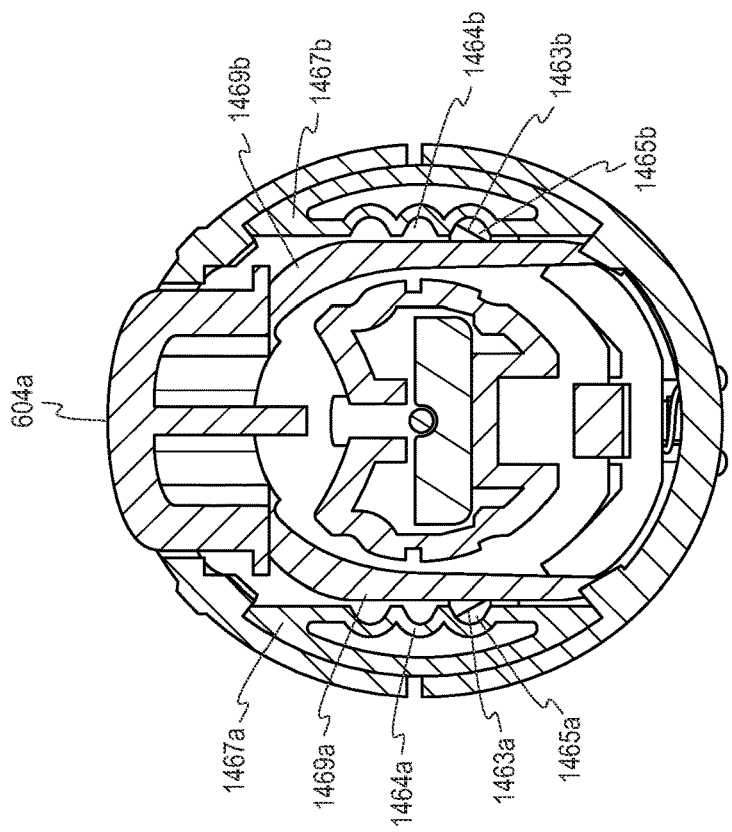
FIGS. 14C and 14D illustrate cross-sectional views of another delivery tool similar to the delivery tool of FIGS. 13A-13D.
Figure 14C:
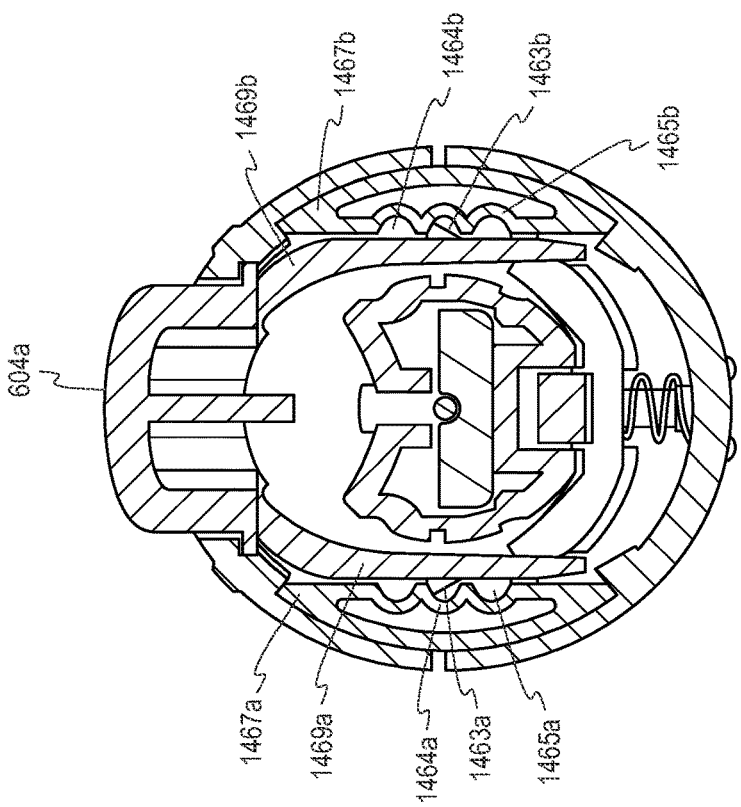

FIGS. 14C and 14D show another exemplary embodiment in which the button 604a includes bilateral connection linkages that engage with discrete positions on bilateral button detent inserts. The embodiment is similar to the embodiment of FIGS. 14A-14B except that the detent bumps 1463a,b on the arms 1469a,b are ramped to decrease the required force to depress the button. Additionally, the reliefs 1464a,b and 1465a,b have dome shapes to provide for stronger holding. Further, the detent insert tabs 1467a,b can each have a semi-circular or D shape, where the straight edge of the D deflects outwards during deployment (as shown by the arrows in FIG. 14D). Similar to the embodiment of FIGS. 14A and 14B, the detent bumps 1463a,b can move from the higher reliefs 1464a,b to the lower reliefs 1465a,b when transitioning from the primed (FIG. 14C) to the deployed (FIG. 14D) configuration. The lower detents 1465a,b can hold the button 604a,b in the down/depressed configuration until it is reset during loading.

The delivery tools described herein can include a number of advantages. For example, the beveled needle tips can allow for tissue plane differentiation for dissecting tissue instead of piercing tissue. The blunter tip of the single bevel cannula can be less likely to penetrate through tissue layers than a sharper distal tip like a cutting trocar beveled tip, can promote easier detection of the intended dissection plane, and can minimize mid-deployment advancement. For example, in the final deployment position over the maxilla, a blunter tip will be less likely than a sharper tip to advance cephalically during deployment of the implant.

The delivery tools described herein also offer improved ergonomics for the user. Minimal or no counter traction needs to be applied on the device due to the deployment mechanics with the outer handle being used for implant advancement. The use of the outer handle to actuate the plunger also reduces the potential for needle withdrawal from the tissue during implant deployment and inadvertently moving the nasal implant from the desired implant location and orientation.

The delivery tool described herein also allow for improved single handed device operation. The delivery tools described herein enable use of the device with minimal manipulation of the tool used to deploy the implant. While holding the device by the grip, the physician can position the needle at the desired location in the soft tissue. Once ready for deployment, the user can readily reach and depress the distal button (e.g. deployment actuator button) with minimal to no manipulation of their hand grip followed by sliding forward the outer handle as gripped to push the nasal implant through the needle to deploy the implant in the targeted location. The one-handed use is beneficial because it helps avoid rotation and deflection of the delivery device during use.

Further, actuation and retraction locks in the devices described herein can be designed to prevent premature deployment. Shrouds around the buttons can likewise be used to prevent inadvertent deployment of the device during use.

It is to be understood that any feature(s) described herein with respect to one embodiment can be combined with or substituted for any feature(s) described herein with respect to another embodiment.

The delivery tools described herein can alternatively or additionally include features that are described in U.S. application Ser. No. 15/274,986, filed Sep. 23, 2016, titled "NASAL IMPLANTS AND SYSTEMS AND METHOD OF USE", the entirety of which is incorporated by reference herein.

In some embodiments, a nasal implant positioning guide can be used when delivering a nasal implant with any of the delivery tools described herein.

FIGS. 15A-15F illustrate external guides that can be used for planning the location and orientation of the implant relative to the nasal anatomy. The nasal implant guides 1400 can each include a handle 1412 and a nasal implant guide portion 1410 (e.g., having an image of a nasal implant on one or both sides thereof to indicate the direction of deployment). The nasal implant guides 1400 can further each include a proximal opening 1402 and a distal opening 1406. The nasal implant guides 1400 can include a forked feature 1408 projecting distally from the distal opening 1406. In some embodiments, the nasal implant guides 1400 can further include a plurality of markings 1404 (e.g., six small bosses thereon) adjacent the proximal opening 1402 adapted to provide a ruler for a user to judge a distance between the proximal feature and an alar rim edge. These markings 1404 can start 4 mm from the center of the ball end, which corresponds with the proximal opening 1402, and can be spaced 2 mm apart. In some embodiments, the handle 1412 can be engaged and axially aligned with the nasal implant guide portion 1410. In other embodiments, the handle 1412 can be engaged with the nasal implant guide portion 1410 such that the handle 1412 forms about a 90 degree angle to a dominant axis of the nasal implant guide portion 1410.

Figure 15A:
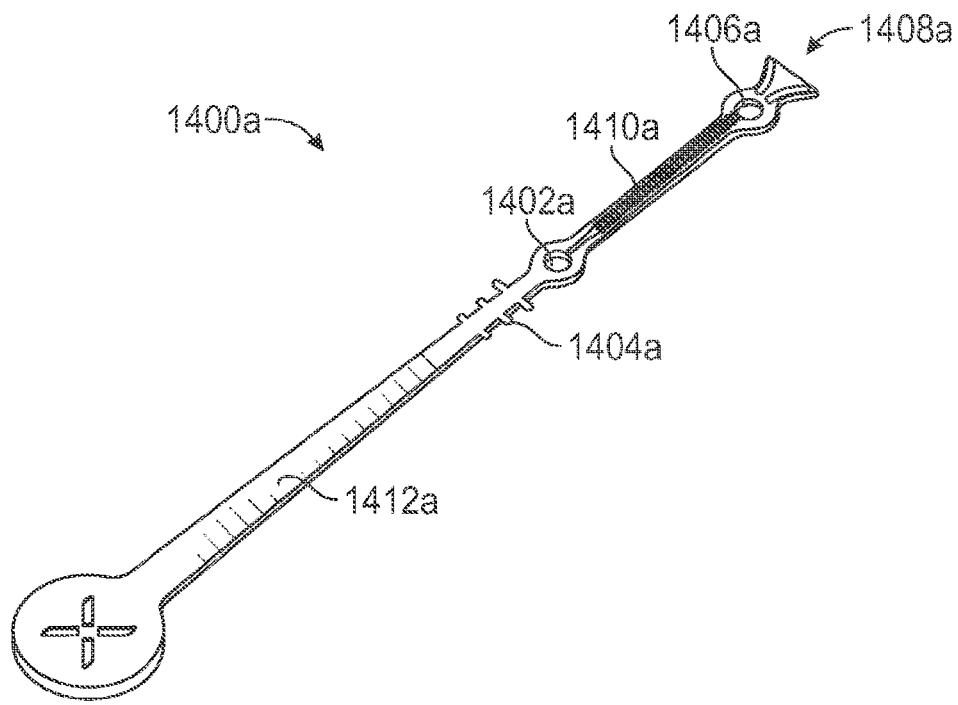
FIGS. 15A-15E illustrate different embodiments of exemplary external nasal guides that a healthcare provider can use for planning the location and orientation of a nasal implant relative to the nasal anatomy.
Figure 15B:
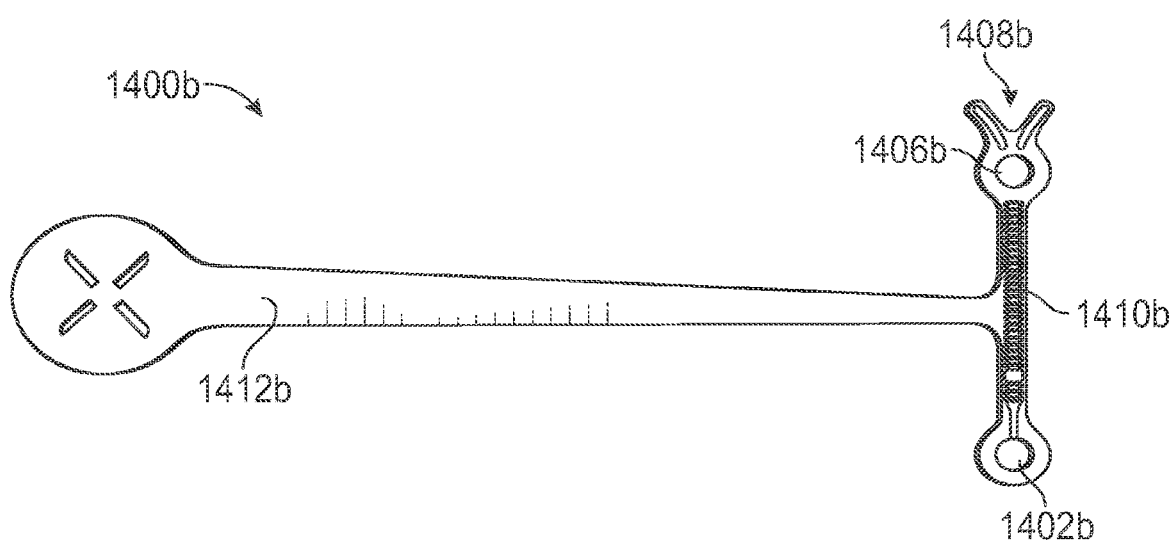
Figure 15C:
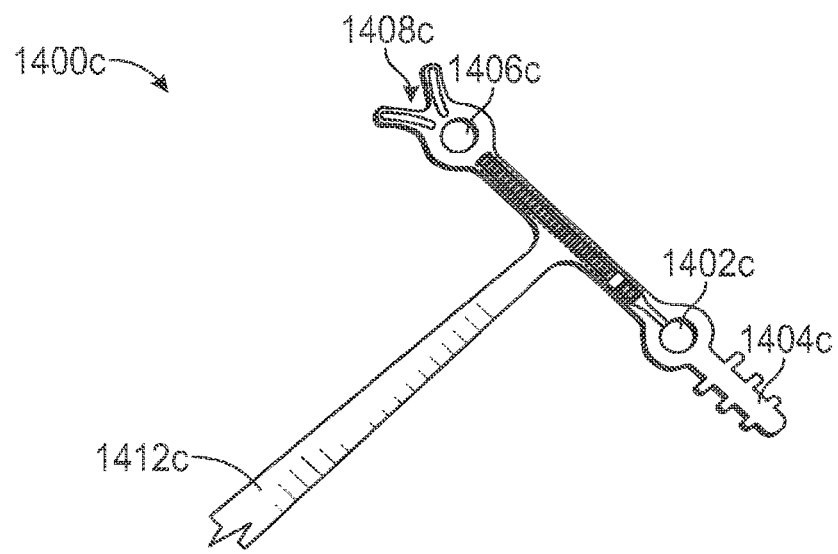
Figure 15D:
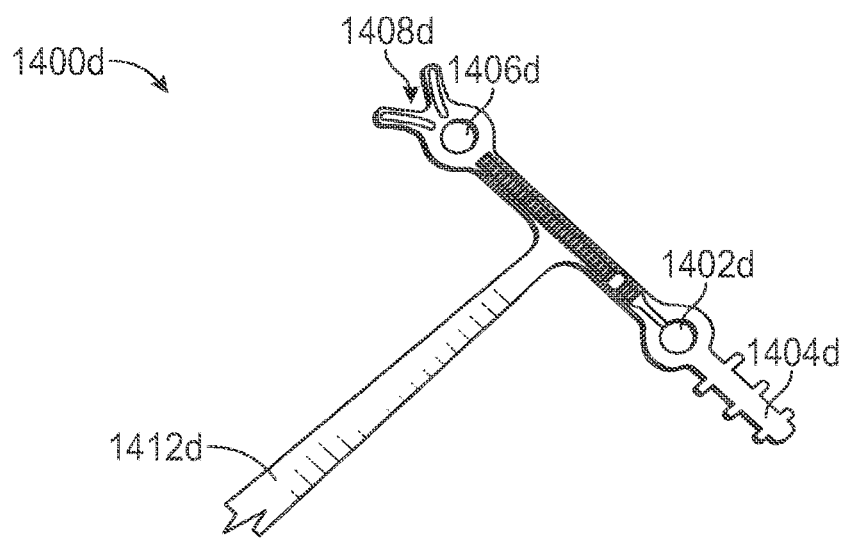
Figure 15E:
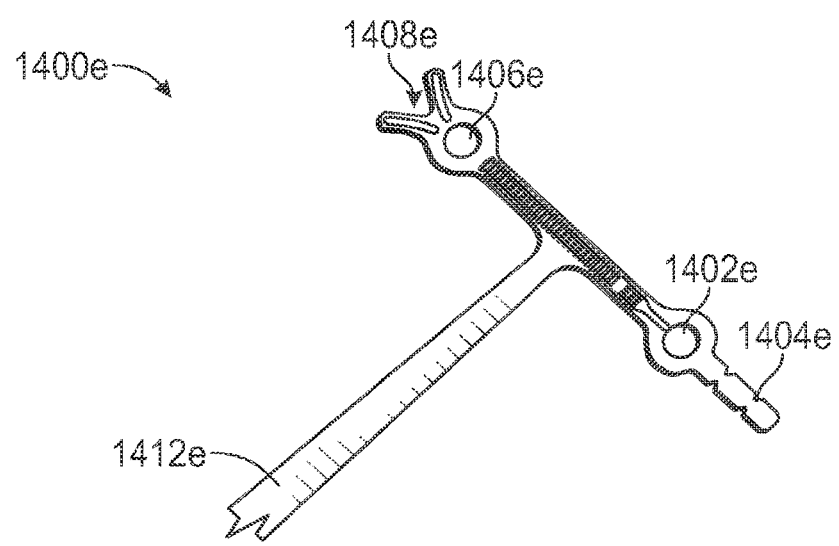

FIG. 15A shows an implant 1400a with the handle 1412a and implant guide portion 1410a axially aligned. FIG. 15B illustrates a guide 1400b with the handle 1412b at a 90 degree angle relative to the guide portion 1410b. The proximal opening 1402b and distal opening 1406b are further larger than the openings 1402a and 1406a to accommodate larger marking pen tips. The forked feature 408b of the aid guide 1410b is configured to contour with the shape of the implant forks to make the implant fork positioning clearer. No markings are shown in device 1400b. FIG. 15C shows a device 1400c with markings 1404c in the forms of bumps at 4 mm, 6 mm, and 8 mm. FIG. 15D includes markings 1404d in the forms of bumps at 4 mm, 8 mm, and 12 mm. FIG. 15E includes markings 1404e in the forms of cut ticks at 4 mm, 8 mm, and 12 mm.

The location of the handle 1412 at a 90 degree angle relative to the guide portion 1412 (as shown in FIGS. 15B-15C) can, in some instances, enable the user to hold the tool about the patient's face to promote better visibility of the target anatomy than when holding it in line with the intended trajectory. The 90-degree design can allow users of left or right handedness to use the guide 1400 while operating on either side of the nasal anatomy.

The nasal implant guides described herein can be used as a planning/marking aid and can be intended to mimic the implant and help the physician map out their preferred implant position. For example, as shown in FIGS. 16A-16B, the nasal implant guide 1600 can be used to guide placement of the implant 1632 (which can be any implant described herein). Like guide 1500a, guide 1600 has a handle 1612 that is axially aligned with the guide portion 1610. As shown in FIG. 16A, the guide 1600 can be positioned such that the user can hold the handle 1612 and make a mark (e.g., with a surgical pen) on the nasal lateral wall through the distal opening 1606 to indicate the desired position of the distal end of the needle of the delivery tool (while the forked features 1608 can correspond to the positioning of the distal forked arms 1676a,b of the implant 1632). Similarly, the user can make a mark on the nasal lateral wall through the proximal opening 1602 to indicate the desired positioning of the proximal feature 1674 of the implant 1632. The markings 1604 can advantageously be used to act as a ruler to visualize the distance of the proximal feature 1674 of the implant from the alar rim edge 1660. The length of the handle 1612 can be designed to keep the user's hand out of the way to provide visualization of the guide 1600 and anatomy during planning/marking.

As shown in FIG. 16B, the markings of the guide 1600 can be used to position the nasal implant 1632 within the nasal anatomy 1665 such that the forked arms 1676a,b are positioned adjacent and across the maxilla bone and the central bridging region 1642 is positioned to support and upper and lower lateral cartilage.

Referring to FIGS. 17A-17B, a nasal implant 1700 can be similarly placed on the nasal anatomy 1735 to help with positioning of the implant 1732 within the nasal anatomy 1735.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A nasal implant delivery tool comprising:
   an inner handle including a loading chamber configured to receive a nasal implant;
   an outer handle configured to move axially relative to the inner handle;
   a needle extending distally from the inner handle, the needle having a central lumen and a distal opening; and
   a push rod configured to move the nasal implant from the loading chamber, through the central lumen, and out the distal opening of the needle, wherein the push rod is coupled to the outer handle such that the push rod moves axially relative to the inner handle when the outer handle is moved axially relative to the inner handle,
   wherein the outer handle is configured to sheath the inner handle,
   wherein the outer handle is configured to move distally relative to the inner handle to cover the loading chamber, and
   wherein the outer handle is configured to move proximally relative to the inner handle to expose the loading chamber for receiving the nasal implant.

2. The nasal implant delivery tool of claim 1, wherein the loading chamber comprises a recess in the inner handle, and wherein the recess is defined by a plurality of side walls and a bottom wall.

3. The nasal implant delivery tool of claim 1, wherein the outer handle is in movable in a proximal direction to a retracted position relative to the inner handle, and
   wherein, when the outer handle is at the retracted position, a portion of the inner handle that includes the loading chamber is distal of a distalmost end of the outer handle.

4. The nasal implant delivery tool of claim 3, wherein, when the outer handle is at the retracted position, the push rod is proximal of the loading chamber.

5. The nasal implant delivery tool of claim 4, wherein, when the outer handle is at the retracted position, at least a portion of the push rod extends into the inner handle to a point that is proximal of the loading chamber.

6. The nasal implant delivery tool of claim 4, wherein the outer handle is movable distally from the retracted position such that the portion of the inner handle and the loading chamber are received in a cavity of the outer handle.

7. The nasal implant delivery tool of claim 6, wherein, when the outer handle is moved distally from the retracted position, the push rod extends through the loading chamber.

8. The nasal implant delivery tool of claim 3, wherein the inner handle comprises a retraction stop tang and the inner handle comprises a stop tooth, and
   wherein, when the outer handle is in the retracted position, the retraction stop tang and the stop tooth engage each other to prevent the inner handle and the outer handle from becoming completely separated.

9. The nasal implant delivery tool of claim 1, wherein the outer handle is configured to move distally relative to the inner handle to cause the push rod to move the nasal implant from the loading chamber, through the central lumen, and out the distal opening of the needle.

10. The nasal implant delivery tool of claim 1, wherein the outer handle moves axially relative to the inner handle via rails that slide over bearing surfaces.

11. The nasal implant delivery tool of claim 1, wherein the needle comprises a tip having a tri-bevel faceted configuration, which includes three surfaces that are each beveled.

12. The nasal implant delivery tool of claim 11, wherein each of the three surfaces are beveled at 45 degrees from a primary bevel orthogonal plane of the tip.

13. The nasal implant delivery tool of claim 11, wherein the tip can have a primary angle between 11 degrees and 15 degrees.

14. The nasal implant delivery tool of claim 1, wherein the needle comprises a tip, and wherein the tip comprises two beveled surfaces that meet in a sharp pointed end.

15. The nasal implant delivery tool of claim 14, wherein the two beveled surfaces can each be beveled at 45 degrees.

16. The nasal implant delivery tool of claim 14, wherein the tip can have a primary angle between 11 degrees and 20 degrees.

17. A method of operating a nasal implant delivery tool, comprising:

moving an outer handle of the nasal implant delivery tool in a proximal direction relative to an inner handle of the nasal implant delivery tool, wherein the moving the outer handle in the proximal direction relative to the inner handle comprises exposing a loading chamber of the inner handle;

after exposing the loading chamber of the inner handle, loading a nasal implant into the loading chamber; and after loading the nasal implant into the loading chamber, moving the outer handle in a distal direction relative to the inner handle to cover the loading chamber and cause a push rod to move the nasal implant from the loading chamber through a central lumen of a needle of the nasal implant delivery tool and out a distal opening of the needle, wherein the push rod is coupled to the outer handle, wherein the outer handle is configured to sheath the inner handle when the outer handle is moved in the distal direction relative to the inner handle.

18. The method of claim 17, wherein the loading chamber comprises a recess in the inner handle,
- wherein the recess is defined by a plurality of side walls and a bottom wall, and
- wherein loading the nasal implant into the loading chamber comprises receiving the nasal implant through a top opening that is (i) defined by the plurality of side walls and (ii) opposite the bottom wall.

19. The method of claim 17, wherein moving the outer handle in the proximal direction relative to the inner handle comprises pulling the push rod proximally away from the loading chamber such that the push rod is clear of the loading chamber.

20. The method of claim 19, wherein moving the outer handle in the distal direction relative to the inner handle comprises moving the push rod through the loading chamber and into the central lumen of the needle.

* * * * *